United States Patent
Scanlan

(10) Patent No.: US 11,578,032 B2
(45) Date of Patent: *Feb. 14, 2023

(54) DERIVATIVES OF SOBETIROME

(71) Applicant: OREGON HEALTH & SCIENCE UNIVERSITY, Portland, OR (US)

(72) Inventor: Thomas Scanlan, Portland, OR (US)

(73) Assignee: OREGON HEALTH & SCIENCE UNIVERSITY, Portland, OR (US)

( * ) Notice: Subject to any disclaimer, the term of this patent is extended or adjusted under 35 U.S.C. 154(b) by 37 days.

This patent is subject to a terminal disclaimer.

(21) Appl. No.: 16/969,793

(22) PCT Filed: Feb. 13, 2019

(86) PCT No.: PCT/US2019/017881
§ 371 (c)(1),
(2) Date: Aug. 13, 2020

(87) PCT Pub. No.: WO2019/160980
PCT Pub. Date: Aug. 22, 2019

(65) Prior Publication Data
US 2021/0002208 A1  Jan. 7, 2021

Related U.S. Application Data

(60) Provisional application No. 62/631,442, filed on Feb. 15, 2018, provisional application No. 62/630,775, filed on Feb. 14, 2018.

(51) Int. Cl.
*C07C 233/40* (2006.01)
*C07C 233/11* (2006.01)
*C07C 233/13* (2006.01)
*C07C 233/22* (2006.01)

(52) U.S. Cl.
CPC .......... *C07C 233/40* (2013.01); *C07C 233/11* (2013.01); *C07C 233/13* (2013.01); *C07C 233/22* (2013.01)

(58) Field of Classification Search
CPC .............................. C07C 233/11; A61P 25/28
USPC ........................................................ 514/563
See application file for complete search history.

(56) References Cited

U.S. PATENT DOCUMENTS

| 5,883,294 A | 3/1999 | Scanlan et al. |
| 9,701,650 B2 | 7/2017 | Scanlan et al. |

FOREIGN PATENT DOCUMENTS

| RU | 2007148927 A | 7/2009 |
| WO | 2017015360 A1 | 1/2017 |
| WO | 2017201320 A1 | 11/2017 |

OTHER PUBLICATIONS

EP19754827.4, "Extended European Search Report", dated Nov. 15, 2021, 9 pages.
Ferrara et al., "Ester-to-Amide Rearrangement of Ethanolamine-Derived Prodrugs of Sobetirome with Increased Blood-Brain Barrier Penetration", Bioorganic & Medicinal Chemistry, vol. 25, No. 10, Mar. 23, 2017, pp. 2743-2753.
Meinig et al., "Targeting Fatty-Acid Amide Hydrolase with Prodrugs for CNS-Selective therapy", ACS Chemical Neuroscience vol. 8, Jul. 30, 2017, 2468-2476.
CN201980015169.5, "Office Action", dated Apr. 2, 2021, 11 pages.
Berge et al., "Pharmaceutical Salts", Journal of Pharmaceutical Sciences, vol. 66, Issue 1, Jan. 1977, pp. 1-19.
Calza et al., "Thyroid hormone and remyelination in adult central nervous system: a lesson from an inflammatory-demyelinating disease", Brain Res Brain Res Rev. 48(2), Apr. 2005, 339-346.
Chiellini et al., "A High-Affinity Subtype-Selective Agonist Ligand for the Thyroid Hormone Receptor", Chemistry & Biology, vol. 5, No. 6, 1998, pp. 299-306.
Grover et al., "Effects of the Thyroid Hormone Receptor Agonist GC-1 on Metabolic Rate and Cholesterol in Rats and Primates: Selective Actions Relative to 3,5,3'-Triiodo-L-Thyronine", Endocrinology, vol. 145, No. 4, Apr. 2004, pp. 1656-1661.
Malm et al., "Recent advances in the development of agonists selective for beta1-type thyroid hormone receptor", Mini Rev Med Chem 7(1), Jan. 2007, 79-86.
O'Shea et al., "Characterization of Skeletal Phenotypes of Tralpha1 and Trbeta Mutant Mice: Implications for Tissue Thyroid Status and T3 Target Gene Expression", Nuclear Receptor Signaling, vol. 4, 2006, 5 pages.
PCT/US2019/017881, International Preliminary Report on Patentability, dated Jul. 24, 2020, 5 pages.
PCT/US2019/017881, International Search Report and Written Opinion, dated May 13, 2019, 9 pages.
Placzek et al., "New Synthetic Routes to Thyroid Hormone Analogs: d6-Sobetirome, 3H-Sobetirome, and the Antagonist NH-3", Tetrahedron, vol. 71, No. 35, Sep. 2, 2015, pp. 5946-5951.
Trost et al., "The Thyroid Hormone Receptor-β-Selective Agonist GC-1 Differentially Affects Plasma Lipids and Cardiac Activity", Endocrinology, vol. 141, No. 9, Sep. 1, 2000, pp. 3057-3064.
Yen, "Physiological and Molecular Basis of Thyroid Hormone Action", Physiological Reviews, vol. 81, No. 3, Jul. 2001, pp. 1097-1142.

(Continued)

*Primary Examiner* — Ana Z Muresan
(74) *Attorney, Agent, or Firm* — Kilpatrick Townsend & Stockton LLP

(57) ABSTRACT

Compounds are provided that function as thyromimetics, which compounds have utility for treating diseases such as neurodegenerative disorders. Pharmaceutical compositions containing such compounds are also provided, as are methods of their use and preparation. Such compounds have the structure of Formula (I) as shown herein, or a pharmaceutically acceptable isomer, racemate, hydrate, solvate, isotope or salt thereof.

24 Claims, No Drawings
Specification includes a Sequence Listing.

(56) References Cited

OTHER PUBLICATIONS

CN201980015169.5, "Office Action", dated Dec. 27, 2021, 7 pages.
IN202017039574, "Office Action", dated Feb. 24, 2022, 7 pages.
CN201980015169.5, "Office Action", dated Jul. 12, 2022, 3 pages.
IL276592, "Office Action", dated Jul. 13, 2022, 4 pages.
MX/A/2020/008498, "Office Action", dated Sep. 5, 2022, 3 pages.
RU2020129983, "Office Action", dated Jun. 20, 2022, 44 pages.

DERIVATIVES OF SOBETIROME

CROSS REFERENCE TO RELATED APPLICATIONS

This application is a National Stage of International Application No. PCT/US2019/017881 filed Feb. 13, 2019, which claims priority to U.S. Provisional Application No. 62/630,775 filed Feb. 14, 2018, and claims priority to U.S. Provisional Application No. 62/631,442 filed Feb. 15, 2018, the contents of which are incorporated by reference in their entirety.

TECHNICAL FIELD

The invention relates to thyromimetic compounds and to products containing the same, as well as to methods of their use and preparation.

BACKGROUND OF THE INVENTION

Thyroid hormone (TH) is a key signal for oligodendrocyte differentiation and myelin formation during development, and also stimulates remyelination in adult models of multiple sclerosis (MS) (Calzà L et al, *Brain Res Revs* 48:339-346, 2005). However, TH is not an acceptable long-term therapy due to there being virtually no therapeutic window in which remyelination can be achieved while avoiding the cardiotoxicity and bone demineralization associated with chronic hyperthyroidism. Some thyroid hormone analogs can activate thyroid hormone-responsive genes while avoiding the associated downsides of TH by exploiting molecular and physiological features of thyroid hormone receptors (Malm J et al, *Mini Rev Med Chem* 7:79-86, 2007). These receptors are expressed in two major forms with heterogenous tissue distributions and overlapping but distinct sets of target genes (Yen P M, *Physiol Rev* 81:1097-1142, 2001). TRα is enriched in the heart, brain, and bone while TRβ is enriched in the liver (O'Shea P J et al, *Nucl Recept Signal* 4:e011, 2006).

Developing selective thyromimetics has been challenging due to the high sequence homology of thyroid hormone receptor subtypes; namely, only one amino acid residue on the internal surface of the ligand binding domain cavity varies between the α1 and β1 forms. GC-1 was one of the first potent analogs that demonstrated significant TRβ-selectivity in vitro (Chiellini G et al, *Chem Biol* 5:299-306, 1998; Yoshihara H A I et al, *J Med Chem* 46:3152-3161, 2003) and in vivo (Trost S U et al, *Endocrinology* 141:3057-3064, 2000; Grover G J et al, *Endocrinology* 145:1656-1661, 2004; Baxter J D et al, *Trends Endocrinol Metab* 15:154-157, 2004).

While progress has been made in this field, there remains a need in the art for further thyromimetic compounds, as well as to products containing the same, and for methods related to their use and preparation.

BRIEF SUMMARY OF THE INVENTION

Disclosed herein are compounds according to Formula (I):

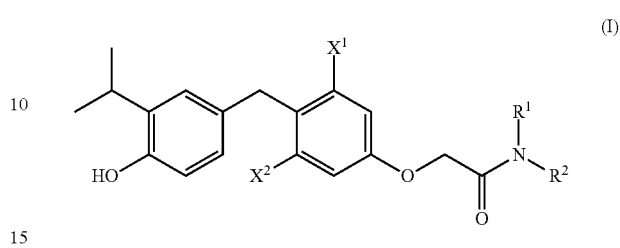

or a pharmaceutically acceptable isomer, racemate, hydrate, solvate, isotope, or salt thereof, wherein $X^1$, $X^2$, $R^1$, and $R^2$ are as defined below.

In an embodiment, a pharmaceutical composition is provided comprising a pharmaceutically effective amount of a compound having the structure of Formula (I), or a pharmaceutically acceptable isomer, racemate, hydrate, solvate, isotope, or salt thereof, in combination with a pharmaceutically acceptable carrier, diluent, or excipient. In an embodiment, the pharmaceutical composition is for use in treating a neurodegenerative disorder including neurodegenerative disorders classified as a demyelinating disease such as X-linked adrenoleukodystrophy or multiple sclerosis.

In an embodiment, a method is provided for treating a neurodegenerative disorder in a subject in need thereof, comprising administering a pharmaceutically effective amount of a compound having the structure of Formula (I), or a pharmaceutically acceptable salt thereof, or a pharmaceutical composition comprising the same. In some aspects, the neurodegenerative disorder can be classified as a demyelinating disease such as X-linked adrenoleukodystrophy or multiple sclerosis.

DETAILED DESCRIPTION OF THE INVENTION

As mentioned above, the invention relates to thyromimetic compounds, to products comprising the same, and to methods for their use and synthesis. The amide compounds of the present invention may act as substrates for the specific hydrolase enzyme fatty acid-amide hydrolase (FAAH), which cleaves the amide, liberating the thyromimetic. Thus, prodrug conversion to drug is enhanced in tissues that express high levels of FAAH such as the central nervous system.

In one embodiment, compounds are provided having the structure of Formula (I), or a pharmaceutically acceptable isomer, racemate, hydrate, solvate, isotope, or salt thereof:

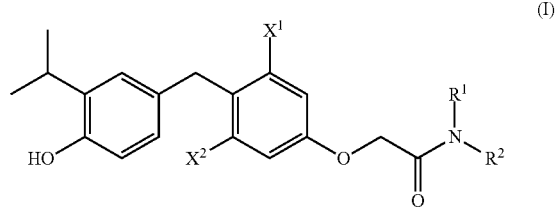

wherein:
X$^1$ and X$^2$ are independently chlorine or bromine;
R$^1$ and R$^2$ are independently hydrogen, —OR$^a$, —NR$^a$R$^b$, alkyl, alkenyl, alkynyl, carbocycle, carbocylealkyl, heterocycle or heterocyclealkyl, wherein each alkyl, carbocycle, carbocylealkyl, heterocycle or heterocyclealkyl is optionally substituted with one or more of halo, cyano, —OR$^a$, —NR$^a$R$^b$, —S(O)$_2$R$^a$ or —S(O)$_2$OR$^a$; and
each R$^a$ and R$^b$ is independently hydrogen or alkyl;
with the proviso that when R$^1$ is hydrogen and both X$^1$ and X$^2$ are bromine or both X$^1$ and X$^2$ are chlorine, R$^2$ is not methyl.

In another embodiment, compounds are provided having the structure of Formula (I), or a pharmaceutically acceptable isomer, racemate, hydrate, solvate, isotope, or salt thereof:

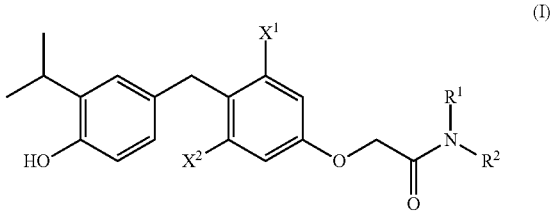

(I)

wherein:
X$^1$ and X$^2$ are independently chlorine or bromine;
R$^1$ and R$^2$ are independently hydrogen, —OR$^a$, —NR$^a$R$^b$, C$_1$-C$_6$ alkyl, C$_2$-C$_6$ alkenyl, C$_2$-C$_6$ alkynyl, C$_3$-C$_6$ carbocycle, C$_3$-C$_6$ carbocylealkyl, 3- to 6-membered heterocycle or 3- to 6-membered heterocyclealkyl, wherein each C$_1$-C$_6$ alkyl, C$_3$-C$_6$ carbocycle, C$_3$-C$_6$ carbocylealkyl, 3- to 6-membered heterocycle or 3- to 6-membered heterocyclealkyl is optionally substituted with 1, 2, 3, or 4 substituents selected from the group of halo, cyano, —OR$^a$, —NR$^a$R$^b$, —S(O)$_2$R$^a$ and —S(O)$_2$OR$^a$; and
each R$^a$ and R$^b$ is independently hydrogen or C$_1$-C$_6$ alkyl;
with the proviso that when R$^1$ is hydrogen and both X$^1$ and X$^2$ are bromine or both X$^1$ and X$^2$ are chlorine, R$^2$ is not methyl.

In a further embodiment comprising compounds of Formula (I), or a pharmaceutically acceptable salt thereof, herein, R$^a$ and R$^b$ are in each appearance independently selected from the group of hydrogen and C$_1$-C$_4$ alkyl. In another embodiment R$^a$ and R$^b$ are in each appearance independently selected from the group of hydrogen and C$_1$-C$_3$ alkyl.

Unless specifically defined otherwise, the technical terms, as used herein, have their normal meaning as understood in the art. The following explanations of terms and methods are provided to better describe the present compounds, compositions and methods, and to guide those of ordinary skill in the art in the practice of the present disclosure. It is also to be understood that the terminology used in the disclosure is for the purpose of describing particular embodiments and examples only and is not intended to be limiting.

As used herein, the singular terms "a," "an," and "the" include plural referents unless context clearly indicates otherwise. Similarly, the word "or" is intended to include "and" unless the context clearly indicates otherwise. Also, as used herein, the term "comprises" means "includes." Hence "comprising A or B" means including A, B, or A and B.

As used herein, "alkyl" means a straight chain or branched saturated hydrocarbon group. "Lower alkyl" means a straight chain or branched alkyl group having from 1 to 8 carbon atoms (C$_1$-C$_8$ alkyl), in some embodiments from 1 to 6 carbon atoms (C$_1$-C$_6$ alkyl), in some embodiments from 1 to 3 carbon atoms (C$_1$-C$_3$ alkyl), in some embodiments from 1 to 4 carbon atoms (C$_1$-C$_4$ alkyl), and in some embodiments from 1 to 2 carbon atoms (C$_1$-C$_2$ alkyl). Examples of straight chain lower alkyl groups include, but are not limited to, methyl, ethyl, n-propyl, n-butyl, n-pentyl, n-hexyl, n-heptyl, and n-octyl groups. Examples of branched lower alkyl groups include, but are not limited to, isopropyl, iso-butyl, sec-butyl, t-butyl, neopentyl, isopentyl, and 2,2-dimethylpropyl groups.

As used herein, "alkenyl" means a straight or branched chain alkyl group as defined above, except that at least one double bond exists between two carbon atoms. Thus, alkenyl groups have from 2 to about 20 carbon atoms (C$_2$-C$_{20}$ alkenyl), and typically from 2 to 12 carbons (C$_2$-C$_{12}$ alkenyl) or, in some embodiments, from 2 to 8 carbon atoms (C$_2$-C$_8$ alkenyl), 2 to 6 carbon atoms (C$_2$-C$_6$ alkenyl), 2 to 4 carbon atoms (C$_2$-C$_4$ alkenyl) or 2 to 3 carbon atoms (C$_2$-C$_3$ alkenyl). Examples include, but are not limited to —CH=CH(CH$_3$), —CH=C(CH$_3$)$_2$, —C(CH$_3$)=CH$_2$, —C(CH$_3$)=CH(CH$_3$), —C(CH$_2$CH$_3$)=CH$_2$, vinyl, butadienyl, pentadienyl, and hexadienyl, among others.

As used herein, "alkynyl" means a straight or branched chain alkyl group as defined above, except that at least one triple bond exists between two carbon atoms. Thus, alkynyl groups have from 2 to about 20 carbon atoms (C$_2$-C$_{20}$ alkynyl), and typically from 2 to 12 carbons (C$_2$-C$_{12}$ alkynyl) or, in some embodiments, from 2 to 8 carbon atoms (C$_2$-C$_8$ alkynyl), 2 to 6 carbon atoms (C$_2$-C$_6$ alkynyl), 2 to 4 carbon atoms (C$_2$-C$_4$ alkynyl), or 2 to 3 carbon atoms (C$_2$-C$_3$ alkynyl). Examples include, but are not limited to —C≡CH, —C≡C(CH$_3$), —C≡C(CH$_2$CH$_3$), —CH$_2$C≡CH, —CH$_2$C≡C(CH$_3$), and —CH$_2$C≡C(CH$_2$CH$_3$), among others.

The terms "carbocyclic" and "carbocycle" denote a ring structure wherein the atoms of the ring are carbon. Carbocycles may be monocyclic or polycyclic. Carbocycle encompasses both saturated and unsaturated rings. Carbocycle encompasses both cycloalkyl and aryl groups. In some embodiments, the carbocycle has 3 to 8 ring members, whereas in other embodiments the number of ring carbon atoms is 4, 5, 6, or 7. Unless specifically indicated to the contrary, the carbocyclic ring can be substituted with as many as N substituents wherein N is the size of the carbocyclic ring with, for example, amino, hydroxy, cyano, carboxy, nitro, thio, alkoxy, and halogen groups.

Cycloalkyl groups are alkyl groups forming a ring structure, which can be substituted or unsubstituted. Examples of cycloalkyl include, but are not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 3 to 6, or 3 to 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined above. Representative substituted cycloalkyl groups can be mono-substituted or substituted more than once, such as, but not limited to, 2,2-, 2,3-, 2,4- 2,5- or 2,6-disubstituted cyclohexyl groups or mono-, di- or tri-substituted norbornyl or cycloheptyl groups, which can be substituted with, for example, amino, hydroxy, cyano, carboxy, nitro, thio, alkoxy, and halogen groups.

Aryl groups are cyclic aromatic hydrocarbons that do not contain heteroatoms. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain 6-14 carbons in the ring portions of the groups. The phrase "aryl groups" includes groups containing fused rings, such as fused aromatic-aliphatic ring systems (e.g., indanyl, tetrahydronaphthyl, and the like). In one embodiment "aryl" is selected from phenyl and naphthyl groups.

As used herein, "carbocyclealkyl" is an alkyl group as defined above in which a hydrogen or carbon bond of the alkyl group is replaced with a bond to a carbocycle group as defined above.

(Cycloalkyl)alkyl groups, also denoted cycloalkylalkyl, are alkyl groups as defined above in which a hydrogen or carbon bond of the alkyl group is replaced with a bond to a cycloalkyl group as defined above.

Aralkyl groups are alkyl groups as defined above in which a hydrogen or carbon bond of an alkyl group is replaced with a bond to an aryl group as defined above. Representative aralkyl groups include benzyl and phenylethyl groups and fused (cycloalkylaryl)alkyl groups such as 4-ethyl-indanyl. Aralkyl groups may also be defined as —$(CH_2)_n$-phenyl, wherein n is an integer selected from 1, 2, and 3 and the phenyl group may be substituted by 0, 1, 2, 3, 4, or 5 substituents selected from amino, hydroxy, cyano, carboxy, nitro, thio, alkoxy, and halogen groups.

The terms "halogen" and "halo" refers to F, Cl, Br, or I.

As used herein, "heterocycle" or "heterocyclyl" groups include aromatic and non-aromatic ring compounds (heterocyclic rings) containing 3 or more ring members, of which one or more is a heteroatom such as, but not limited to, N, O, S, or P. A heterocyclyl group as defined herein can be a heteroaryl group or a partially or completely saturated cyclic group including at least one ring heteroatom. In some embodiments, heterocyclyl groups include 3 to 20 ring members, whereas other such groups have 3 to 15 ring members. At least one ring contains a heteroatom, but every ring in a polycyclic system need not contain a heteroatom. For example, a dioxolanyl ring and a benzdioxolanyl ring system (methylenedioxyphenyl ring system) are both heterocyclyl groups within the meaning herein. A heterocyclyl group designated as a $C_2$-heterocyclyl can be a 5-membered ring with two carbon atoms and three heteroatoms, a 6-membered ring with two carbon atoms and four heteroatoms and so forth. Likewise a $C_4$-heterocyclyl can be a 5-membered ring with one heteroatom, a 6-membered ring with two heteroatoms, and so forth. The number of carbon atoms plus the number of heteroatoms sums up to equal the total number of ring atoms. A saturated heterocyclic ring refers to a heterocyclic ring containing no unsaturated carbon atoms. In one embodiment, "heterocycle" or "heterocyclyl" groups comprise 3- to 6-membered rings in which 0, 1, or 2 ring atoms may be a heteroatom selected from O, S, and N. Examples of heterocyclyl groups include oxiranyl, oxetanyl, tetrahydrofuranyl, tetrahydropyranyl, tetrahydrothiophenyl, tetrahydropyranyl, pyrrolidinyl, piperidinyl, pyrimidinyl, piperazinyl, imidazolidinyl, and morpholinyl groups.

Heteroaryl groups are aromatic ring compounds containing 5 or more ring members, of which one or more is a heteroatom such as, but not limited to, N, O, and S. A heteroaryl group designated as a $C_2$-heteroaryl can be a 5-membered ring with two carbon atoms and three heteroatoms, a 6-membered ring with two carbon atoms and four heteroatoms and so forth. Likewise a $C_4$-heteroaryl can be a 5-membered ring with one heteroatom, a 6-membered ring with two heteroatoms, and so forth. The number of carbon atoms plus the number of heteroatoms sums up to equal the total number of ring atoms. Heteroaryl groups include, but are not limited to, groups such as pyrrolyl, pyrazolyl, triazolyl, tetrazolyl, oxazolyl, isoxazolyl, thiazolyl, pyridinyl, thiophenyl, benzothiophenyl, benzofuranyl, indolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, tetrahydroisoquinolinyl, quinoxalinyl, and quinazolinyl groups. The terms "heteroaryl" and "heteroaryl groups" include fused ring compounds such as wherein at least one ring, but not necessarily all rings, are aromatic, including tetrahydroquinolinyl, tetrahydroisoquinolinyl, indolyl and 2,3-dihydro indolyl.

As used herein, "heterocyclealkyl" is an alkyl group as defined above in which a hydrogen or carbon bond of the alkyl group is replaced with a bond to a heterocycle group as defined above. Examples of heterocyclealkyl groups include —$(CH_2)_n$-oxiranyl, —$(CH_2)_n$-oxetanyl, —$(CH_2)_n$-tetrahydrofuranyl, —$(CH_2)_n$-tetrahydropyranyl, —$(CH_2)_n$-tetrahydrothiophenyl, —$(CH_2)_n$-tetrahydropyranyl, —$(CH_2)_n$-pyrrolidinyl, —$(CH_2)_n$-piperidinyl, —$(CH_2)_n$-pyrimidinyl, —$(CH_2)_n$-piperazinyl, —$(CH_2)_n$-imidazolidinyl, and —$(CH_2)_n$-morpholinyl groups, wherein in each instance "n" represents an integer selected from 1, 2, and 3.

As used herein, the term "optionally substituted" refers to a group (e.g., an alkyl, alkenyl, alkynyl, carbocycle, carbocylealkyl, heterocycle or heterocyclealkyl) having 0, 1, or more substituents, such as 0-25, 0-20, 0-10, 0-5, 0-4, 0-3, or 0-2 substituents. It is understood that each range includes each whole number integer in the range, such as 0-3 referring to a range of 0, 1, 2, or 3 substituents. Substituents include, but are not limited to, halo, cyano, —$OR^a$, —$NR^aR^b$, —$S(O)_2R^a$ or —$S(O)_2OR^a$, wherein each $R^a$ and $R^b$ is, independently, H or $C_1$-$C_6$ alkyl.

In another embodiment, $R^1$ is hydrogen and compounds are provided having the structure of Formula (II), or a pharmaceutically acceptable isomer, racemate, hydrate, solvate, isotope, or salt thereof:

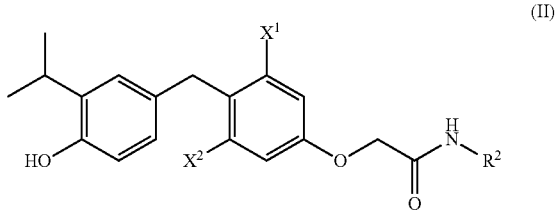

(II)

wherein:
  $X^1$ and $X^2$ are independently chlorine or bromine;
  $R^2$ is selected from the group of hydrogen, —$OR^a$, —$NR^aR^b$, alkyl, alkenyl, alkynyl, carbocycle, carbocylealkyl, heterocycle or heterocyclealkyl, wherein each alkyl, carbocycle, carbocylealkyl, heterocycle or heterocyclealkyl is optionally substituted with one or more of halo, cyano, —$OR^a$, —$NR^aR^b$, $S(O)_2R^a$ or —$S(O)_2OR^a$; and each $R^a$ and $R^b$ are independently hydrogen or alkyl;
with the proviso that when both $X^1$ and $X^2$ are bromine or both $X^1$ and $X^2$ are chlorine, $R^2$ is not methyl.

In another embodiment, $R^1$ is hydrogen and compounds are provided having the structure of Formula (II), or a pharmaceutically acceptable isomer, racemate, hydrate, solvate, isotope, or salt thereof:

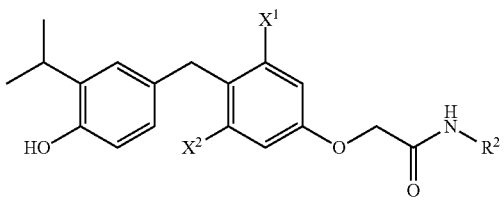

wherein:
$X^1$ and $X^2$ are independently chlorine or bromine;
$R^2$ is selected from the group of hydrogen, —$OR^a$, —$NR^aR^b$, $C_1$-$C_6$ alkyl, $C_2$-$C_6$ alkenyl, $C_2$-$C_6$ alkynyl, $C_3$-$C_6$ carbocycle, $C_3$-$C_6$ carbocylealkyl, 3- to 6-membered heterocycle and 3- to 6-membered heterocyclealkyl, wherein each $C_1$-$C_6$ alkyl, $C_2$-$C_6$ alkynyl, $C_2$-$C_6$ alkenyl, $C_3$-$C_6$ carbocycle, $C_3$-$C_6$ carbocylealkyl, 3- to 6-membered heterocycle or 3- to 6-membered heterocyclealkyl is optionally substituted with one or more substituents selected from the group of halo, cyano, —$OR^a$, —$NR^aR^b$, $S(O)_2R^a$ and —$S(O)_2OR^a$; and
each $R^a$ and $R^b$ are independently hydrogen or $C_1$-$C_6$ alkyl;
with the proviso that when both $X^1$ and $X^2$ are bromine or both $X^1$ and $X^2$ are chlorine, $R^2$ is not methyl.

Also provided is a compound of Formula (II), or a pharmaceutically acceptable isomer, racemate, hydrate, solvate, isotope, or salt thereof:

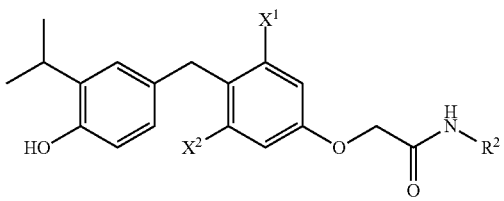

wherein:
$X^1$ and $X^2$ are independently chlorine or bromine;
$R^2$ is selected from the group of hydrogen, —$OR^a$, —$NR^aR^b$, $C_1$-$C_4$ alkyl, $C_2$-$C_4$ alkenyl, $C_2$-$C_4$ alkynyl, $C_3$-$C_6$ carbocycle, $C_3$-$C_6$ carbocylealkyl, 3- to 6-membered heterocycle or 3- to 6-membered heterocyclealkyl, wherein each $C_1$-$C_4$ alkyl, $C_3$-$C_6$ carbocycle, $C_3$-$C_6$ carbocylealkyl, 3- to 6-membered heterocycle or 3- to 6-membered heterocyclealkyl is optionally substituted with 0, 1, 2, 3, or 4 substituents selected from the group of halo, cyano, —$OR^a$, —$NR^aR^b$, $S(O)_2R^a$ and —$S(O)_2OR^a$; and
each $R^a$ and $R^b$ are independently hydrogen or $C_1$-$C_4$ alkyl;
with the proviso that when both $X^1$ and $X^2$ are bromine or both $X^1$ and $X^2$ are chlorine, $R^2$ is not methyl.

Also provided is a compound of Formula (II), or a pharmaceutically acceptable isomer, racemate, hydrate, solvate, isotope, or salt thereof:

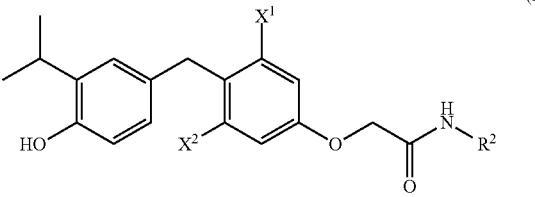

wherein:
$X^1$ and $X^2$ are independently chlorine or bromine;
$R^2$ is selected from the group of OH, —O—($C_1$-$C_4$ alkyl), $C_1$-$C_4$ alkyl, $C_2$-$C_4$ alkenyl, $C_2$-$C_4$ alkynyl, —$NH_2$, —NH ($C_1$-$C_4$ alkyl), —N($C_1$-$C_4$ alkyl)$_2$, —$(CH_2)_n$—$C_3$-$C_6$ cycloalkyl, —$(CH_2)_n$-3- to 6-membered heterocycle, —$SO_3H$, —$SO_2$—$C_1$-$C_4$ alkyl, and

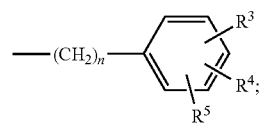

each of the $C_1$-$C_4$ alkyl groups in the $R^2$—O—($C_1$-$C_4$ alkyl), $C_1$-$C_4$ alkyl, —NH($C_1$-$C_4$ alkyl), —N($C_1$-$C_4$ alkyl)$_2$, —$SO_3H$, and —$SO_2$—$C_1$-$C_4$ alkyl groups is substituted by 0, 1, 2, 3, or 4 substituents selected from OH and halogen,
n in each instance is an integer independently selected from 0, 1, 2, and 3; and
$R^3$, $R^4$, and $R^5$ are each independently selected from hydrogen, halogen, and OH.

Also provided is a compound of Formula (II), or a pharmaceutically acceptable isomer, racemate, hydrate, solvate, isotope, or salt thereof, wherein:
$X^1$ and $X^2$ are independently chlorine or bromine;
$R^2$ is selected from the group of OH, —O—($C_1$-$C_3$ alkyl), $C_1$-$C_3$ alkyl, $C_2$-$C_3$ alkenyl, $C_2$-$C_3$ alkynyl, —$NH_2$, —NH ($C_1$-$C_3$ alkyl), —N($C_1$-$C_3$ alkyl)$_2$, —$(CH_2)_n$—$C_3$-$C_6$ cycloalkyl, —$(CH_2)_n$-3- to 6-membered heterocycle, —$SO_3H$, —$SO_2$—$C_1$-$C_3$ alkyl, and

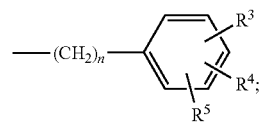

each of the $C_1$-$C_3$ alkyl groups in the $R^2$—O—($C_1$-$C_3$ alkyl), $C_1$-$C_3$ alkyl, —NH($C_1$-$C_3$ alkyl), —N($C_1$-$C_3$ alkyl)$_2$, and —$SO_2$—$C_1$-$C_3$ alkyl groups is substituted by 0, 1, 2, or 3 substituents selected from OH and halogen,
n in each instance is an integer independently selected from 0, 1, 2, and 3; and
$R^3$, $R^4$, and $R^5$ are each independently selected from hydrogen, halogen, and OH.

Also provided is a compound of Formula (II), or a pharmaceutically acceptable isomer, racemate, hydrate, solvate, isotope, or salt thereof, wherein:

$X^1$ and $X^2$ are independently chlorine or bromine; and
$R^2$ is selected from the group of $C_1$-$C_4$ alkyl, $C_2$-$C_4$ alkenyl, and $C_2$-$C_4$ alkynyl.

Also provided is a compound of Formula (II), or a pharmaceutically acceptable isomer, racemate, hydrate, solvate, isotope, or salt thereof, wherein:

$X^1$ and $X^2$ are independently chlorine or bromine; and
$R^2$ is selected from the group of —$NH_2$, —$NH(C_1$-$C_4$ alkyl), and —$N(C_1$-$C_4$ alkyl$)_2$.

Also provided is a compound of Formula (II), or a pharmaceutically acceptable isomer, racemate, hydrate, solvate, isotope, or salt thereof, wherein:

$X^1$ and $X^2$ are independently chlorine or bromine; and
$R^2$ is selected from the group of —$(CH_2)_n$—$C_3$-$C_6$ cycloalkyl and —$(CH_2)_n$-3- to 6-membered heterocycle.

Also provided is a compound of Formula (II), or a pharmaceutically acceptable isomer, racemate, hydrate, solvate, isotope, or salt thereof, wherein:

$X^1$ and $X^2$ are independently chlorine or bromine;
$R^2$ is

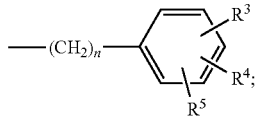

n in each instance is an integer independently selected from 0, 1, 2, and 3; and
$R^3$, $R^4$, and $R^5$ are each independently selected from hydrogen, halogen, and OH.

In one embodiment, compounds having the structure of Formula (I) or Formula (II) are provided where $X^1$ and $X^2$ are both chlorine. In another embodiment, $X^1$ and $X^2$ are both bromine. In another embodiment, $X^1$ is chlorine and $X^2$ is bromine. In another embodiment, $X^1$ is bromine and $X^2$ is chlorine.

In one embodiment, compounds having the structure of Formula (I) or Formula (II) are provided where $R^2$ is hydrogen. In another embodiment, $R^2$ is —$OR^a$. Each W and $R^b$ is independently hydrogen or alkyl. In one embodiment, $R^2$ is —OH or —OMe. In another embodiment, $R^2$ is —$NR^aR^b$. Each $R^a$ and $R^b$ is independently hydrogen or alkyl. In one embodiment, $R^2$ is —$NH_2$.

In another embodiment, $R^2$ is alkyl. In one embodiment, $R^2$ is saturated alkyl. $R^2$ can be, for example, methyl, ethyl, n-propyl, isopropyl, n-butyl, isobutyl, sec-butyl, tert-butyl, n-pentyl, branched pentyl, n-hexyl, or branched hexyl. In some embodiments, $R^2$ is methyl. In another embodiment, $R^2$ is unsaturated alkyl. $R^2$ can be, for example, ethenyl, ethynyl, propenyl, or propynyl. In one embodiment, alkyl is substituted with one or more of halo, cyano, —$OR^a$, —$NR^aR^b$, —$S(O)_2R^a$, or —$S(O)_2OR^a$. Each $R^a$ and $R^b$ is independently hydrogen or alkyl.

In another embodiment, $R^2$ is carbocycle or carbocyclealkyl, each of which is optionally substituted with one or more of halo, cyano, —$OR^a$, —$NR^aR^b$, —$S(O)_2R^a$ or —$S(O)_2OR^a$.

In one embodiment, $R^2$ is cycloalkyl optionally substituted with one or more of halo, cyano, —$OR^a$, —$NR^aR^b$, —$S(O)_2R^a$ or —$S(O)_2OR^a$. In another embodiment, $R^2$ is cycloalkyl substituted with 0, 1, 2, 3, or 4 substituents selected from halo, cyano, —$OR^a$, —$NR^aR^b$, —$S(O)_2R^a$ and —$S(O)_2OR^a$.

In one embodiment, $R^2$ is aryl optionally substituted with one or more of halo, cyano, —$OR^a$, —$NR^aR^b$, —$S(O)_2R^a$ or —$S(O)_2OR^a$. In another embodiment, $R^2$ is aryl substituted with 0, 1, 2, 3, or 4 substituents selected from the group of halo, cyano, —$OR^a$, —$NR^aR^b$, —$S(O)_2R^a$ and —$S(O)_2OR^a$.

In one embodiment, $R^2$ is carbocylealkyl optionally substituted with one or more of halo, cyano, —$OR^a$, —$NR^aR^b$, —$S(O)_2R^a$ or —$S(O)_2OR^a$. In another embodiment, $R^2$ is carbocylealkyl substituted with 0, 1, 2, 3, or 4 substituents selected from the group of halo, cyano, —$OR^a$, —$NR^aR^b$, —$S(O)_2R^a$ and —$S(O)_2OR^a$.

In another embodiment, $R^2$ is heterocycle or heterocyclealkyl, each of which is optionally substituted with one or more of halo, cyano, —$OR^a$, —$NR^aR^b$, —$S(O)_2R^a$ or —$S(O)_2OR^a$. Each $R^a$ and $R^b$ is independently hydrogen or alkyl. In another embodiment, $R^2$ is 3- to 6-membered heterocycle or 3- to 6-membered heterocyclealkyl, each of which is optionally substituted with 0, 1, 2, 3, or 4 substituents selected from halo, cyano, —$OR^a$, —$NR^aR^b$, —$S(O)_2R^a$ and —$S(O)_2OR^a$. Each $R^a$ and $R^b$ is independently hydrogen or alkyl.

Each $R^a$ and $R^b$ in the groups above is independently selected from hydrogen or $C_1$-$C_6$ alkyl. In each of the groups above there is a further embodiment in which each $R^a$ and $R^b$ is independently selected from hydrogen and $C_1$-$C_4$ alkyl. In each of the groups above there is also a further embodiment in which each $R^a$ and $R^b$ is independently selected from hydrogen and $C_1$-$C_3$ alkyl.

In another embodiment, compounds having the structure of Formula (I) are provided where $R^1$ and $R^2$ are alkyl. In one embodiment, $R^1$ and $R^2$ are both methyl.

In a further embodiment comprising compounds of Formula (II), or a pharmaceutically acceptable salt thereof, herein, $R^a$ and $R^b$ are in each appearance independently selected from the group of hydrogen and $C_1$-$C_4$ alkyl. In another embodiment within each group $R^a$ and $R^b$ are in each appearance independently selected from the group of hydrogen and $C_1$-$C_3$ alkyl.

Representative compounds of Formulas (I) and (II) as applicable, include the compounds listed in Table 1 below, as well as pharmaceutically acceptable isomers, racemates, hydrates, solvates, isotopes, and salts thereof.

TABLE 1

Representative Compounds

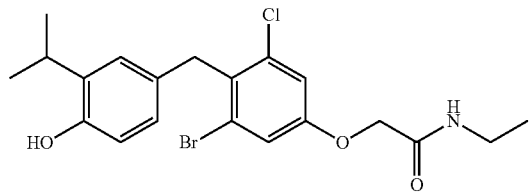 [SMILES: CCNC(=O)COc1cc(Cl)c(Cc2ccc(O)c(C(C)C)c2)c(Br)c1]

1

TABLE 1-continued
Representative Compounds
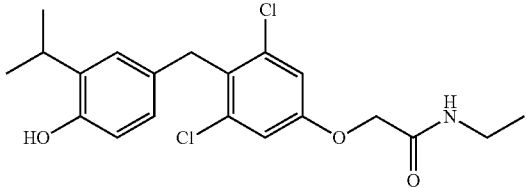
2
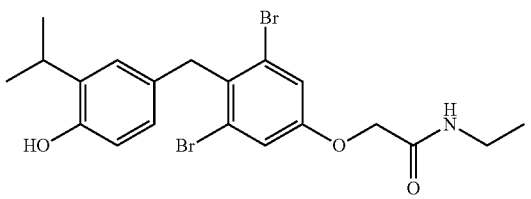
3
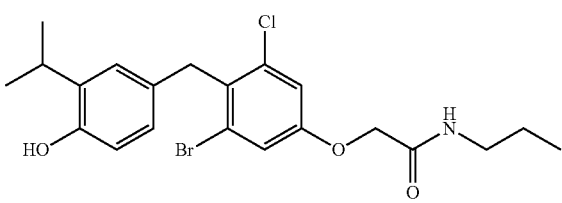
4
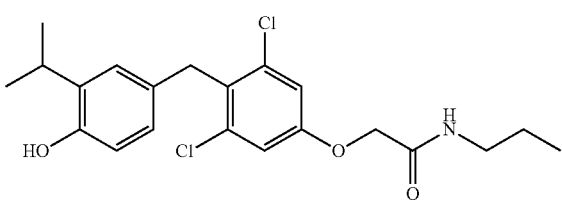
5
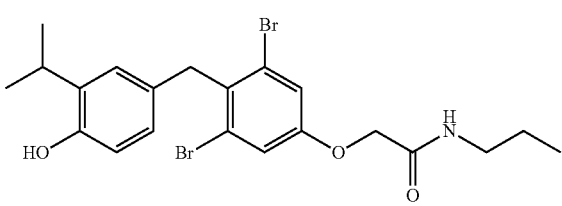 [SMILES: CCCNC(=O)COc1cc(Br)c(Cc2ccc(O)c(C(C)C)c2)c(Br)c1]
6
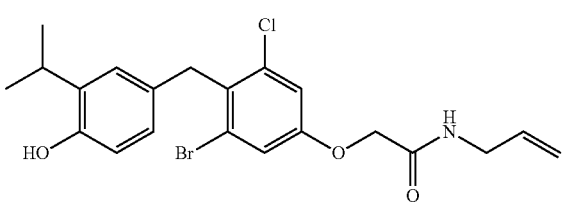 [SMILES: C=CCNC(=O)COc1cc(Cl)c(Cc2ccc(O)c(C(C)C)c2)c(Br)c1]
7
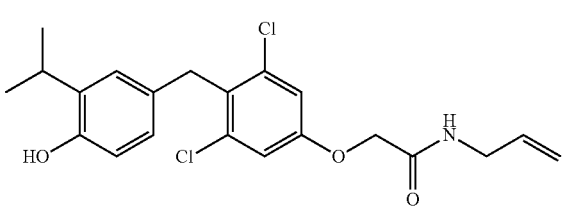 [SMILES: C=CCNC(=O)COc1cc(Cl)c(Cc2ccc(O)c(C(C)C)c2)c(Cl)c1]
8

TABLE 1-continued
Representative Compounds
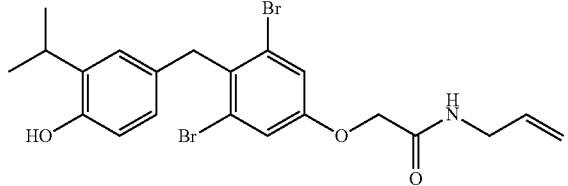 [SMILES: C=CCNC(=O)COc1cc(Br)c(Cc2ccc(O)c(C(C)C)c2)c(Br)c1]
9
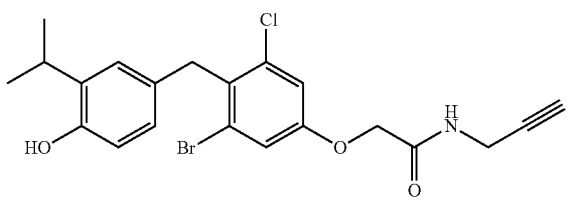
10
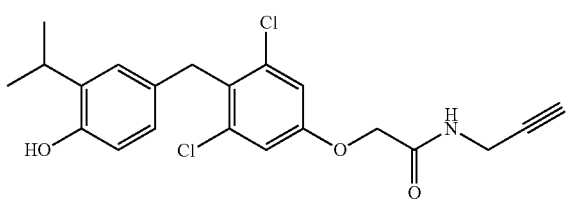 [SMILES: C#CCNC(=O)COc1cc(Cl)c(Cc2ccc(O)c(C(C)C)c2)c(Cl)c1]
11
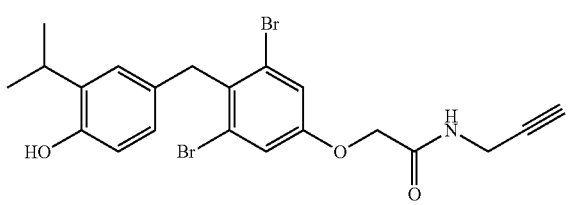 [SMILES: C#CCNC(=O)COc1cc(Br)c(Cc2ccc(O)c(C(C)C)c2)c(Br)c1]
12
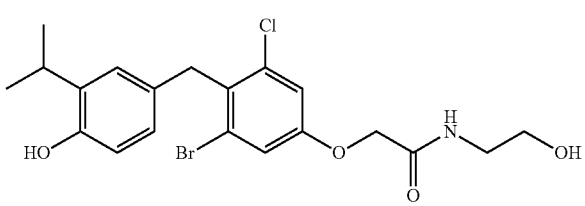
13
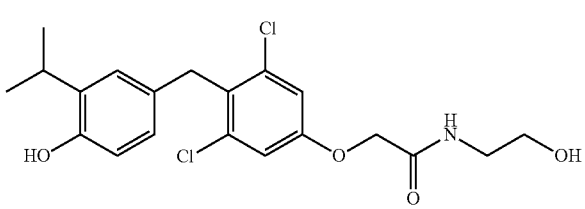 [SMILES: CC(C)c1cc(Cc2c(Cl)cc(OCC(=O)NCCO)cc2Cl)ccc1O]
14
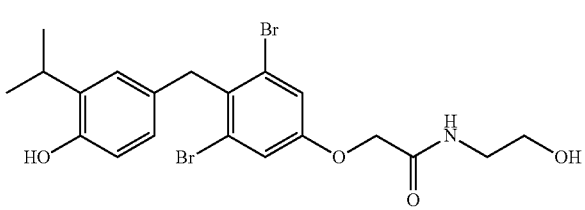 [SMILES: CC(C)c1cc(Cc2c(Br)cc(OCC(=O)NCCO)cc2Br)ccc1O]
15

TABLE 1-continued
Representative Compounds
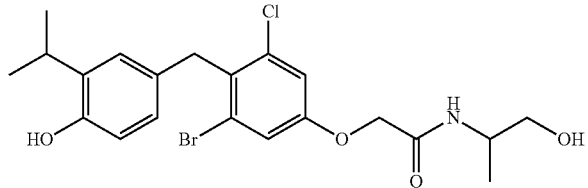 [SMILES: CC(CO)NC(=O)COc1cc(Cl)c(Cc2ccc(O)c(C(C)C)c2)c(Br)c1]
16
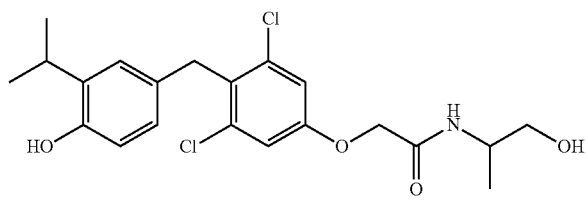 [SMILES: CC(CO)NC(=O)COc1cc(Cl)c(Cc2ccc(O)c(C(C)C)c2)c(Cl)c1]
17
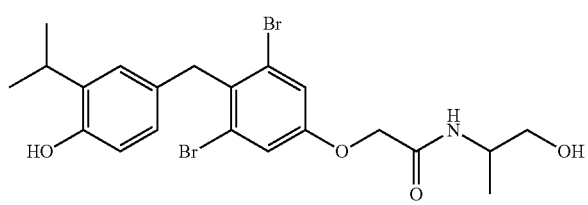 [SMILES: CC(CO)NC(=O)COc1cc(Br)c(Cc2ccc(O)c(C(C)C)c2)c(Br)c1]
18
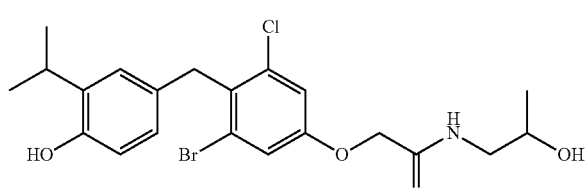
19
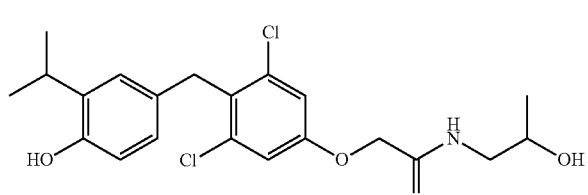
20
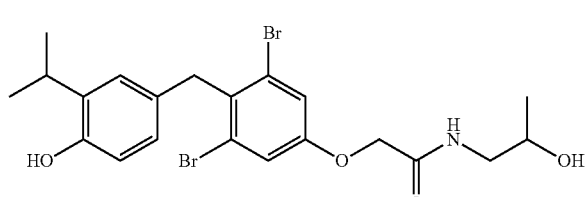
21
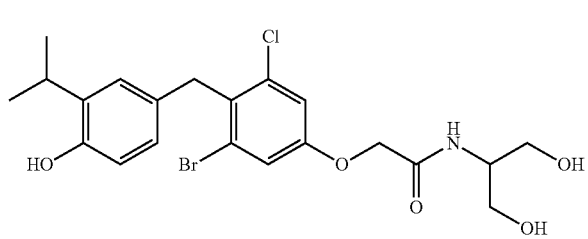
22

TABLE 1-continued
Representative Compounds
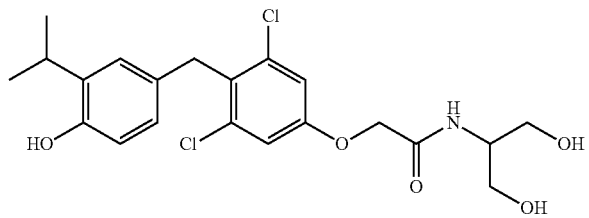 [SMILES: CC(C)c1cc(Cc2c(Cl)cc(OCC(=O)NC(CO)CO)cc2Cl)ccc1O]
23
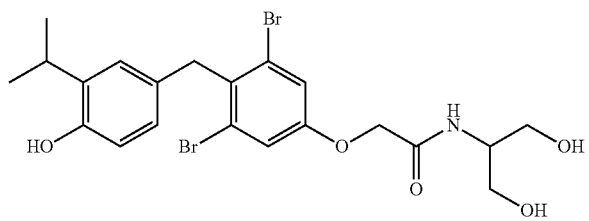 [SMILES: CC(C)c1cc(Cc2c(Br)cc(OCC(=O)NC(CO)CO)cc2Br)ccc1O]
24
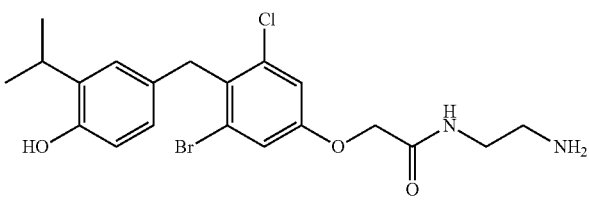
25
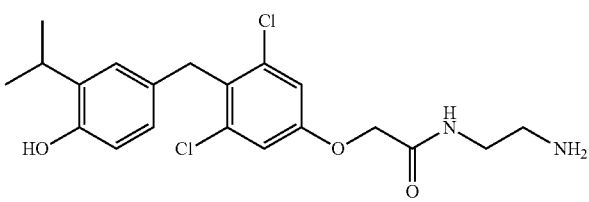 [SMILES: CC(C)c1cc(Cc2c(Cl)cc(OCC(=O)NCCN)cc2Cl)ccc1O]
26
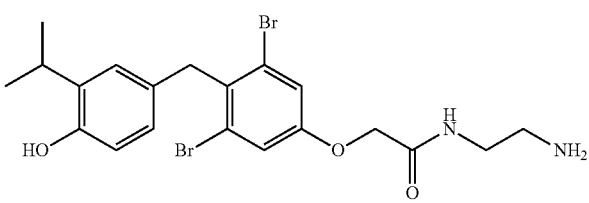 [SMILES: CC(C)c1cc(Cc2c(Br)cc(OCC(=O)NCCN)cc2Br)ccc1O]
27
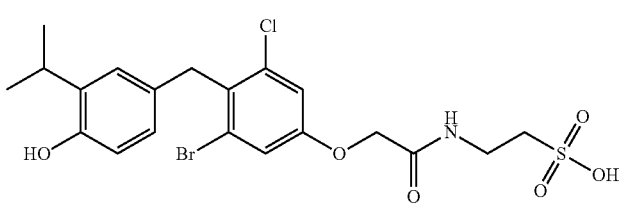 [SMILES: CC(C)c1cc(Cc2c(Cl)cc(OCC(=O)NCCS(=O)(=O)O)cc2Br)ccc1O]
28
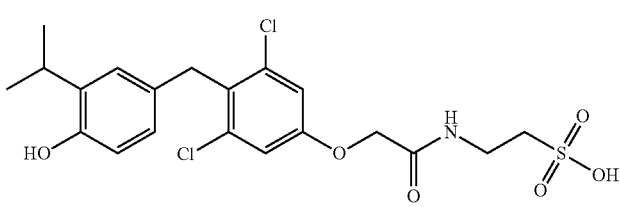 [SMILES: CC(C)c1cc(Cc2c(Cl)cc(OCC(=O)NCCS(=O)(=O)O)cc2Cl)ccc1O]
29

TABLE 1-continued
Representative Compounds
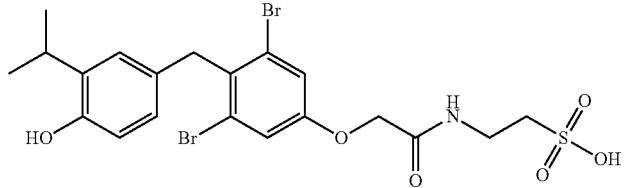 [SMILES: CC(C)c1cc(Cc2c(Br)cc(OCC(=O)NCCS(=O)(=O)O)cc2Br)ccc1O] 30
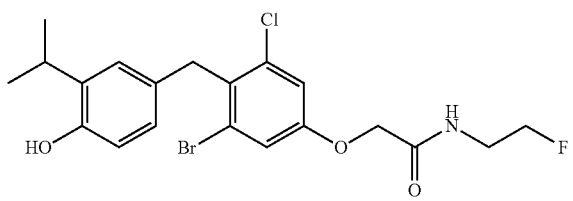 31
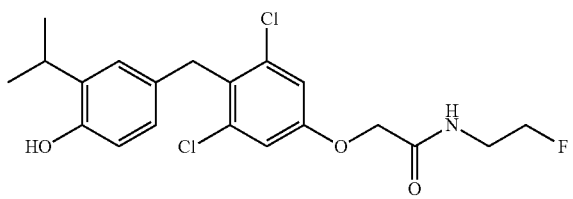 32
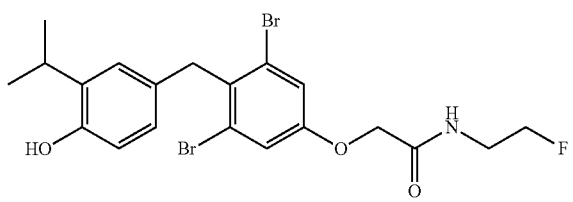 [SMILES: CC(C)c1cc(Cc2c(Cl)cc(OCC(=O)NCCF)cc2Br)ccc1O] 33
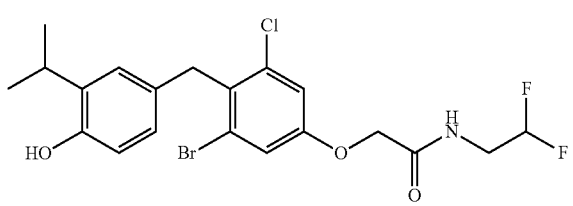 34
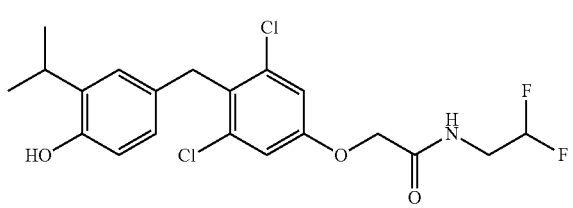 [SMILES: CC(C)c1cc(Cc2c(Cl)cc(OCC(=O)NCC(F)F)cc2Cl)ccc1O] 35
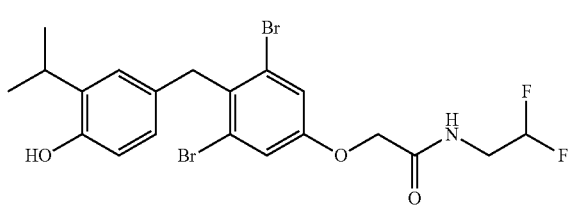 [SMILES: CC(C)c1cc(Cc2c(Br)cc(OCC(=O)NCC(F)F)cc2Br)ccc1O] 36

TABLE 1-continued

Representative Compounds

| | |
|---|---|
| (structure: 4-hydroxy-3-isopropylbenzyl linked to 2-chloro-6-bromophenyl-O-CH2-C(O)-NH-CH2-CF3) | 37 |
| (structure: 4-hydroxy-3-isopropylbenzyl linked to 2,6-dichlorophenyl-O-CH2-C(O)-NH-CH2-CF3) | 38 |
| (structure: 4-hydroxy-3-isopropylbenzyl linked to 2,6-dibromophenyl-O-CH2-C(O)-NH-CH2-CF3) | 39 |
| (structure: 4-hydroxy-3-isopropylbenzyl linked to 2-chloro-6-bromophenyl-O-CH2-C(O)-NH-cyclopropyl) | 40 |
| (structure: 4-hydroxy-3-isopropylbenzyl linked to 2,6-dichlorophenyl-O-CH2-C(O)-NH-cyclopropyl) | 41 |
| (structure: 4-hydroxy-3-isopropylbenzyl linked to 2,6-dibromophenyl-O-CH2-C(O)-NH-cyclopropyl) | 42 |
| (structure: 4-hydroxy-3-isopropylbenzyl linked to 2-chloro-6-bromophenyl-O-CH2-C(O)-NH-oxetan-3-yl) | 43 |

TABLE 1-continued

Representative Compounds

| | |
|---|---|
| (structure: 4-hydroxy-3-isopropylbenzyl linked to 2,6-dichlorophenyl ether-CH$_2$-C(O)NH-oxetan-3-yl) | 44 |
| (structure: 4-hydroxy-3-isopropylbenzyl linked to 2,6-dibromophenyl ether-CH$_2$-C(O)NH-oxetan-3-yl) | 45 |
| (structure: 4-hydroxy-3-isopropylbenzyl linked to 2-chloro-6-bromophenyl ether-CH$_2$-C(O)N(CH$_3$)$_2$) | 46 |
| (structure: 4-hydroxy-3-isopropylbenzyl linked to 2,6-dichlorophenyl ether-CH$_2$-C(O)N(CH$_3$)$_2$) | 47 |
| (structure: 4-hydroxy-3-isopropylbenzyl linked to 2,6-dibromophenyl ether-CH$_2$-C(O)N(CH$_3$)$_2$) | 48 |
| (structure: 4-hydroxy-3-isopropylbenzyl linked to 2-chloro-6-bromophenyl ether-CH$_2$-C(O)NHOH) | 49 |
| (structure: 4-hydroxy-3-isopropylbenzyl linked to 2,6-dichlorophenyl ether-CH$_2$-C(O)NHOH) | 50 |
| (structure: 4-hydroxy-3-isopropylbenzyl linked to 2,6-dibromophenyl ether-CH$_2$-C(O)NHOH) | 51 |

TABLE 1-continued
Representative Compounds
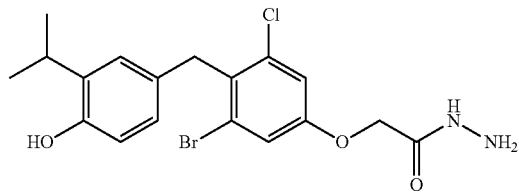 [SMILES: CC(C)c1cc(Cc2c(Cl)cc(OCC(=O)NN)cc2Br)ccc1O]
52
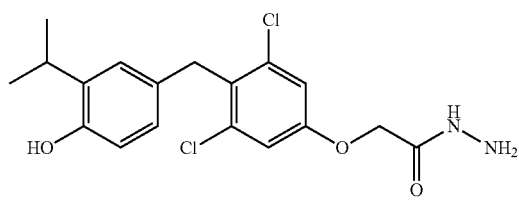 [SMILES: CC(C)c1cc(Cc2c(Cl)cc(OCC(=O)NN)cc2Cl)ccc1O]
53
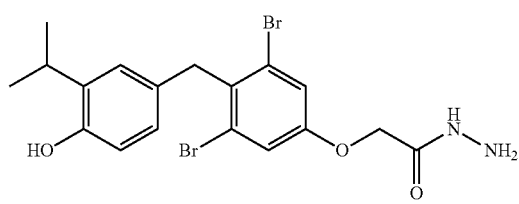 [SMILES: CC(C)c1cc(Cc2c(Br)cc(OCC(=O)NN)cc2Br)ccc1O]
54
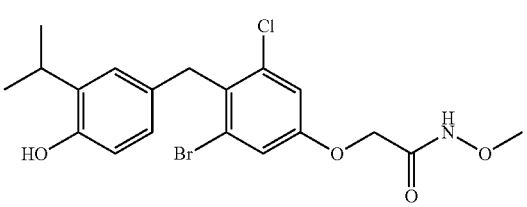 [SMILES: CONC(=O)COc1cc(Br)c(Cc2ccc(O)c(C(C)C)c2)c(Br)c1]
55
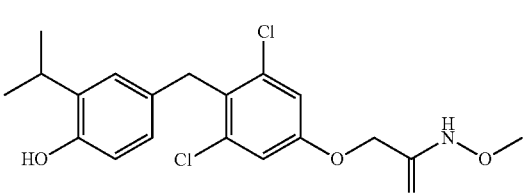
56
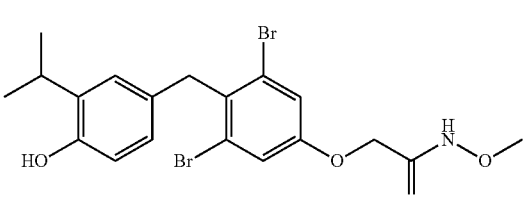
57
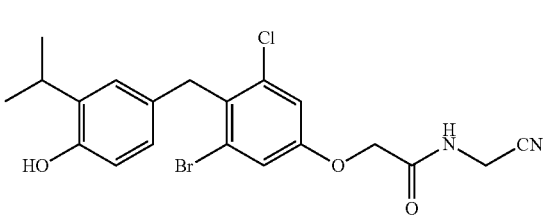
58

TABLE 1-continued
Representative Compounds
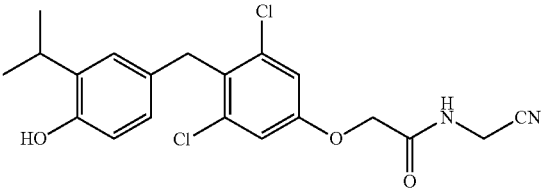 [SMILES: CC(C)c1cc(Cc2c(Cl)cc(OCC(=O)NCC#N)cc2Cl)ccc1O]
59
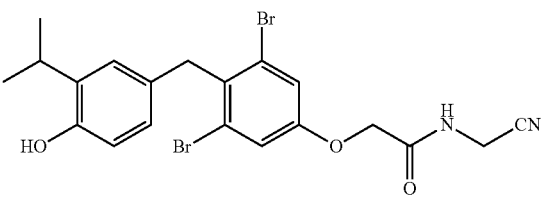 [SMILES: CC(C)c1cc(Cc2c(Br)cc(OCC(=O)NCC#N)cc2Br)ccc1O]
60
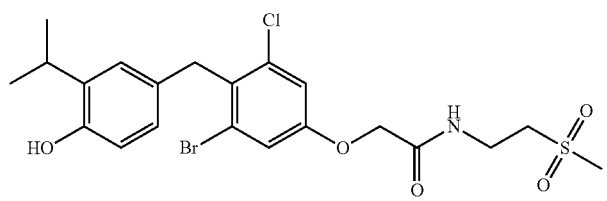 [SMILES: CC(C)c1cc(Cc2c(Cl)cc(OCC(=O)NCCS(C)(=O)=O)cc2Br)ccc1O]
61
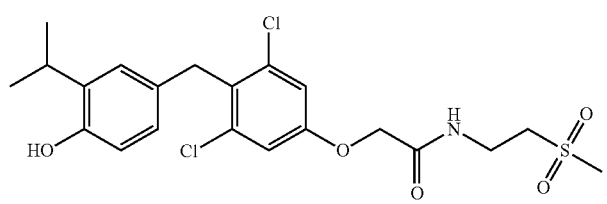
62
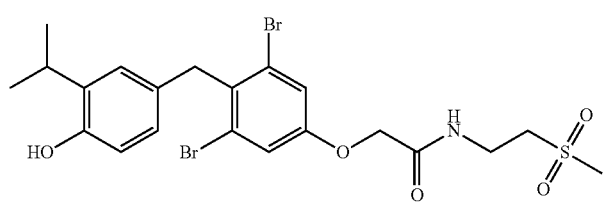 [SMILES: CC(C)c1cc(Cc2c(Br)cc(OCC(=O)NCCS(C)(=O)=O)cc2Br)ccc1O]
63
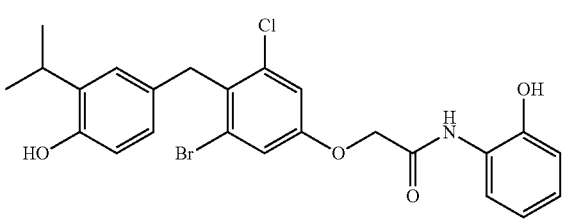 [SMILES: CC(C)c1cc(Cc2c(Cl)cc(OCC(=O)Nc3ccccc3O)cc2Br)ccc1O]
64
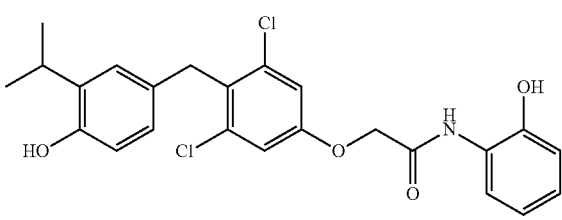 [SMILES: CC(C)c1cc(Cc2c(Cl)cc(OCC(=O)Nc3ccccc3O)cc2Cl)ccc1O]
65

TABLE 1-continued
Representative Compounds
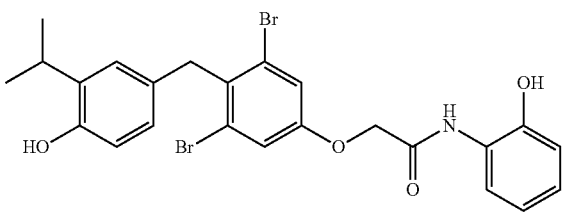 [SMILES: CC(C)c1cc(Cc2c(Br)cc(OCC(=O)Nc3ccccc3O)cc2Br)ccc1O]
66
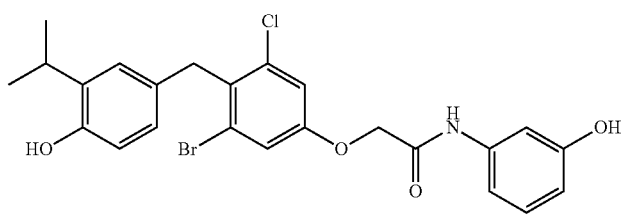 [SMILES: CC(C)c1cc(Cc2c(Cl)cc(OCC(=O)Nc3cccc(O)c3)cc2Br)ccc1O]
67
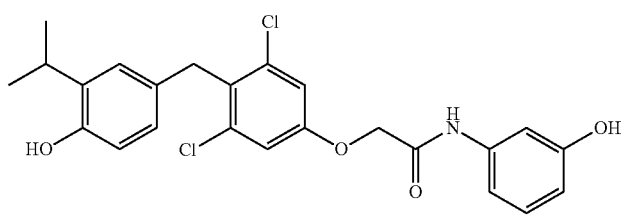 [SMILES: CC(C)c1cc(Cc2c(Cl)cc(OCC(=O)Nc3cccc(O)c3)cc2Cl)ccc1O]
68
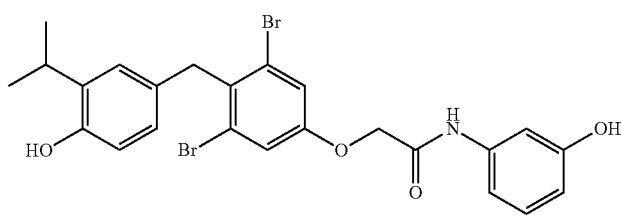 [SMILES: CC(C)c1cc(Cc2c(Br)cc(OCC(=O)Nc3cccc(O)c3)cc2Br)ccc1O]
69
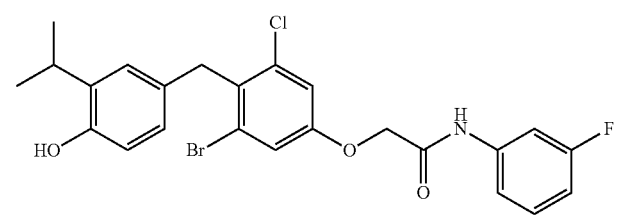 [SMILES: CC(C)c1cc(Cc2c(Cl)cc(OCC(=O)Nc3cccc(F)c3)cc2Br)ccc1O]
70
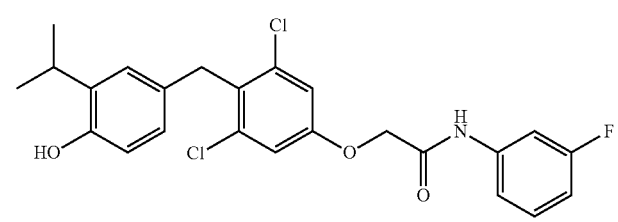
71

TABLE 1-continued

Representative Compounds

| | |
|---|---|
| [Structure of compound 72: 4-((4-hydroxy-3-isopropylbenzyl)-3,5-dibromophenoxy)-N-(3-fluorophenyl)acetamide] | 72 |
| [Structure of compound 73: 4-((4-hydroxy-3-isopropylbenzyl)-3-bromo-5-chlorophenoxy)-N-benzylacetamide] | 73 |
| [Structure of compound 74: 4-((4-hydroxy-3-isopropylbenzyl)-3,5-dichlorophenoxy)-N-benzylacetamide] | 74 |
| [Structure of compound 75: 4-((4-hydroxy-3-isopropylbenzyl)-3,5-dibromophenoxy)-N-benzylacetamide] | 75 |
| [Structure of compound 76: 4-((4-hydroxy-3-isopropylbenzyl)-3-bromo-5-chlorophenoxy)-N-phenethylacetamide] | 76 |
| | 77 |
| [Structure of compound 78: 4-((4-hydroxy-3-isopropylbenzyl)-3,5-dibromophenoxy)-N-phenethylacetamide] | 78 |
| [Structure of compound 79: 4-((4-hydroxy-3-isopropylbenzyl)-3-bromo-5-chlorophenoxy)-N-(2-(3,4-dihydroxyphenyl)ethyl)acetamide] | 79 |

TABLE 1-continued

Representative Compounds

80: [structure: 3-isopropyl-4-hydroxybenzyl linked to 2,6-dichloro-4-(OCH2C(O)NH-CH2CH2-3,4-dihydroxyphenyl)phenyl]

81: [structure: 3-isopropyl-4-hydroxybenzyl linked to 2,6-dibromo-4-(OCH2C(O)NH-CH2CH2-3,4-dihydroxyphenyl)phenyl]

82: [structure: 3-isopropyl-4-hydroxybenzyl linked to 2-bromo-6-chloro-4-(OCH2C(O)NH2)phenyl]

83: [structure: 3-isopropyl-4-hydroxybenzyl linked to 2-bromo-6-chloro-4-(OCH2C(O)NHCH3)phenyl]

All chiral, diastereomeric, racemic forms of a structure are intended, unless a particular stereochemistry or isomeric form is specifically indicated. Compounds used in the present disclosure can include enriched or resolved optical isomers at any or all asymmetric atoms as are apparent from the depictions, at any degree of enrichment. Both racemic and diastereomeric mixtures, as well as the individual optical isomers can be synthesized so as to be substantially free of their enantiomeric or diastereomeric partners, and these are all within the scope of certain embodiments of the disclosure.

A "hydrate" is a compound that exists in a composition with water molecules. The composition can include water in stoichiometric quantities, such as a monohydrate or a dihydrate, or can include water in random amounts. As the term is used herein a "hydrate" refers to a solid form, i.e., a compound in water solution, while it may be hydrated, is not a hydrate as the term is used herein.

A "solvate" is a similar composition except that a solvent other that water replaces the water. For example, methanol or ethanol can form an "alcoholate", which can again be stoichiometric or non-stoichiometric. As the term is used herein a "solvate" refers to a solid form, i.e., a compound in solution in a solvent, while it may be solvated, is not a solvate as the term is used herein.

An "isotope" of a compound of the disclosure is a compound having one or more atoms of the compound replaced by an isotope of such atom. For example, isotopes include compounds with deuterium in place of one or more hydrogen atoms of the compound such as compounds of the disclosure in which the methyl groups of the isopropyl moiety of Formulas (I) and (II) are fully or partially deuterated (e.g., $(D_3C)_2CH—$). Isotopic substitutions which may be made in the formation of isotopes of the disclosure include non-radioactive (stable) atoms such as deuterium and carbon 13, as well as radioactive (unstable) atoms such as tritium, carbon 14, iodine 123, iodine 125, and the like.

As used herein, the term "pharmaceutically acceptable salt" refers to salts prepared by conventional methods. These include basic salts of inorganic and organic acids, such as, without limitation, hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, and mandelic acid. "Pharmaceutically acceptable salts" of the presently disclosed compounds also include those formed from cations such as, without limitation, sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide. These salts may be prepared by standard procedures, for example by reaction of the free acid with a suitable organic or inorganic base. Any chemical compound recited in this specification may alternatively be administered as a pharmaceutically acceptable salt thereof. Pharmaceutically acceptable salts are also inclusive of the free acid, base, and zwitterionic forms of the disclosed compounds. Descriptions of exemplary pharmaceutically acceptable salts can be found in Stahl and Wermuth, Eds., *Handbook of Pharmaceutical Salts; Properties, Selection and Use*, Wiley VCH (2008). When the compounds disclosed herein include an acidic group such as a carboxy group, then suitable pharmaceutically acceptable cation pairs for the carboxy group are well known to those skilled in the art and include, without limitation, alkaline, alkaline earth, ammonium, and quaternary ammonium cations. Such salts are known to those of skill in the art. Similarly when the compounds disclosed herein include a basic group such as an amino group, then suitable pharmaceutically acceptable anion pairs for the basic group are similarly well known and include halide, hydroxide, perhalate, halite, hypohalite, sulfate, sulfite, phosphate, phosphite, nitrate, nitrite, and others known to those of skill in the art. For additional examples of pharmacologically acceptable salts, see Berge et al, *J. Pharm. Sci.* 66, 1 (1977).

In certain embodiments, the invention provides a pharmaceutical composition comprising a compound of the invention together with at least one pharmaceutically acceptable carrier, diluent, or excipient. For example, the active compound will usually be mixed with a carrier, or diluted by a carrier, or enclosed within a carrier which can be in the form of an ampoule, capsule, sachet, paper, or other container. When the active compound is mixed with a carrier, or when the carrier serves as a diluent, it can be solid, semi-solid, or liquid material that acts as a vehicle, excipient, or medium for the active compound. The active compound can be adsorbed on a granular solid carrier, for example contained in a sachet. Some examples of suitable carriers are water, salt solutions, alcohols, polyethylene glycols, polyhydroxyethoxylated castor oil, peanut oil, olive oil, gelatin, lactose, terra alba, sucrose, dextrin, magnesium carbonate, sugar, cyclodextrin, amylose, magnesium stearate, talc, gelatin, agar, pectin, acacia, stearic acid, or lower alkyl ethers of cellulose, silicic acid, fatty acids, fatty acid amines, fatty acid monoglycerides and diglycerides, pentaerythritol fatty acid esters, polyoxyethylene, hydroxymethylcellulose, and polyvinylpyrrolidone. Similarly, the carrier or diluent can include any sustained release material known in the art, such as glyceryl monostearate or glyceryl distearate, alone or mixed with a wax.

As used herein, the term "pharmaceutical composition" refers to a composition containing one or more of the compounds described herein, or a pharmaceutically acceptable isomer, racemate, hydrate, solvate, isotope or salt thereof, formulated with a pharmaceutically acceptable carrier, which can also include other additives, and manufactured or sold with the approval of a governmental regulatory agency as part of a therapeutic regimen for the treatment of disease in a mammal. Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); or in any other formulation described herein. Conventional procedures and ingredients for the selection and preparation of suitable formulations are described, for example, in *Remington: The Science and Practice of Pharmacy*, 21$^{st}$ Ed., Gennaro, Ed., Lippencott Williams & Wilkins (2005) and in The United States Pharmacopeia: The National Formulary (USP 36 NF31), published in 2013.

As used herein, the term "pharmaceutically acceptable carrier" refers to any ingredient other than the disclosed compounds, or a pharmaceutically acceptable isomer, racemate, hydrate, solvate, isotope or salt thereof (e.g., a carrier capable of suspending or dissolving the active compound) and having the properties of being nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, or waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, stearic acid, sucrose, talc, titanium dioxide, vitamin A, vitamin E, vitamin C, and xylitol.

The formulations can be mixed with auxiliary agents which do not deleteriously react with the active compounds. Such additives can include wetting agents, emulsifying and suspending agents, salt for influencing osmotic pressure, buffers and/or coloring substances, preserving agents, sweetening agents, or flavoring agents. The compositions can also be sterilized if desired.

The route of administration can be any route which effectively transports the active compound of the invention to the appropriate or desired site of action, such as oral, nasal, pulmonary, buccal, subdermal, intradermal, transdermal, or parenteral, e.g., rectal, depot, subcutaneous, intravenous, intraurethral, intramuscular, intranasal, ophthalmic solution, or an ointment, the oral route being preferred.

Dosage forms can be administered once a day, or more than once a day, such as twice or thrice daily. Alternatively, dosage forms can be administered less frequently than daily, such as every other day, or weekly, if found to be advisable by a prescribing physician. Dosing regimens include, for example, dose titration to the extent necessary or useful for the indication to be treated, thus allowing the patient's body to adapt to the treatment and/or to minimize or avoid unwanted side effects associated with the treatment. Other dosage forms include delayed or controlled-release forms. Suitable dosage regimens and/or forms include those set out, for example, in the latest edition of the *Physicians' Desk Reference*, incorporated herein by reference.

In another embodiment, there are provided methods of making a composition of a compound described herein including formulating a compound of the invention with a pharmaceutically acceptable carrier or diluent. In some embodiments, the pharmaceutically acceptable carrier or diluent is suitable for oral administration. In some such embodiments, the methods can further include the step of formulating the composition into a tablet or capsule. In other embodiments, the pharmaceutically acceptable carrier or diluent is suitable for parenteral administration. In some such embodiments, the methods further include the step of lyophilizing the composition to form a lyophilized preparation.

In another embodiment, a method of treating a subject having a neurodegenerative disease is provided, the method comprising administering to the subject a pharmaceutically effective amount of a compound having the structure of Formula (I) or (II) or pharmaceutically acceptable isomer, racemate, hydrate, solvate, isotope or salt thereof, or a pharmaceutical composition thereof. In one embodiment, the neurodegenerative disease is a demyelinating disease. In another embodiment, the neurodegenerative disease is X-linked adrenoleukodystrophy or multiple sclerosis. In one embodiment, the neurodegenerative disease is acute disseminated encelphalomyelitis, acute hemorrhagic leukoencephalitis, adult Refsum disease, Alexander disease, Alzheimer's disease, Balo concentric sclerosis, Canavan disease, central pontine myelinolysis, cerebral palsy, cerebrotendineous xanthomatosis, chronic inflammatory demyelinating polyneuropathy, Devic's syndrome, diffuse myelinoclastic sclerosis, Guillain-Barre syndrome, idiopathic inflammatory demyelinating disease, infantile Refsum disease, Krabbe disease, Leber hereditary optic neuropathy, Marburg multiple sclerosis, Marchiafava-Bignami disease, metachromatic leukodystrophy, multifocal motor neuropathy, paraproteinemic demyelinating polyneuropathy, Pelizaeus-Merzbacher disease, peroneal muscular atrophy, progressive multifocal leukoencephalopathy, transverse myelitis, tropical spastic paraparesis, van der Knaap disease, X-linked adrenoleukodystrophy, or Zellweger syndrome.

In another embodiment, a method of treating a subject having Alzheimer's disease is provided, the method comprising administering to the subject a pharmaceutically effective amount of a compound having the structure of Formula (I) or (II) or pharmaceutically acceptable isomer, racemate, hydrate, solvate, isotope or salt thereof, or a pharmaceutical composition thereof.

In another embodiment, a method of treating a subject having acute disseminated encephalomyelitis (ADEM), acute hemorrhagic leukoencephalitis (AHL or AHLE), adult Refsum disease, infantile Refsum disease, Alexander disease, Alzheimer's disease, Balo concentric sclerosis, Canavan disease, central pontine myelinolysis (CPM), cerebral palsy, cerebrotendineous xanthomatosis, chronic inflammatory demyelinating polyneuropathy (CIDP), Devic's syndrome, diffuse myelinoclastic sclerosis, encephalomyelitis, Guillain-Barre syndrome, idiopathic inflammatory demyelinating disease (IIDD), Krabbe disease, Leber hereditary optic neuropathy, leukodystrophy, Marburg multiple sclerosis, Marchiafava-Bignami disease, metachromatic leukodystrophy (MLD), multifocal motor neuropathy (MMN), multiple sclerosis (MS), paraproteinemic demyelinating polyneuropathy, Pelizaeus-Merzbacher disease (PMD), progressive multifocal leukoencephaalopathy (PML), tropical spastic paraparesis (TSP), X-linked adrenoleukodystrophy (X-ALD, ALO, or X-linked ALO), or Zellweger syndrome is provided, the method comprising administering to the subject a pharmaceutically effective amount of a compound having the structure of Formula (I) or (II) or pharmaceutically acceptable isomer, racemate, hydrate, solvate, isotope or salt thereof, or a pharmaceutical composition thereof.

In another embodiment, a compound having the structure of Formula (I) or (II) or pharmaceutically acceptable isomer, racemate, hydrate, solvate, isotope or salt thereof, or a pharmaceutical composition thereof is provided for use in the treatment of a neurodegenerative disease. In one embodiment, the neurodegenerative disease is a demyelinating disease. In another embodiment, the neurodegenerative disease is X-linked adrenoleukodystrophy or multiple sclerosis. In another embodiment, the neurodegenerative disease is acute disseminated encephalomyelitis, acute hemorrhagic leukoencephalitis, adult Refsum disease, Alexander disease, Alzheimer's disease, balo concentric sclerosis, Canavan disease, central pontine myelinolysis, cerebral palsy, cerebrotendineous xanthomatosis, chronic inflammatory demyelinating polyneuropathy, Devic's syndrome, diffuse myelinoclastic sclerosis, Guillain-Barre syndrome, idiopathic inflammatory demyelinating disease, infantile Refsum disease, Krabbe disease, Leber hereditary optic neuropathy, Marburg multiple sclerosis, Marchiafava-Bignami disease, metachromatic leukodystrophy, Multifocal motor neuropathy, paraproteinemic demyelinating polyneuropathy, Pelizaeus-Merzbacher disease, peroneal muscular atrophy, progressive multifocal leukoencephalopathy, transverse myelitis, tropical spastic paraparesis, van der Knaap disease, X-linked adrenoleukodystrophy, or Zellweger syndrome.

In another embodiment, a compound having the structure of Formula (I) or (II) or pharmaceutically acceptable isomer, racemate, hydrate, solvate, isotope or salt thereof, or a pharmaceutical composition thereof is provided for use in the treatment of Alzheimer's disease.

In another embodiment, a compound having the structure of Formula (I) or (II) or pharmaceutically acceptable isomer, racemate, hydrate, solvate, isotope, or salt thereof, or a pharmaceutical composition thereof is provided for use in the treatment of acute disseminated encephalomyelitis (ADEM), acute hemorrhagic leukoencephalitis (AHL or AHLE), adult Refsum disease, infantile Refsum disease, Alexander disease, Alzheimer's disease, Balo concentric sclerosis, Canavan disease, central pontine myelinolysis (CPM), cerebral palsy, cerebrotendineous xanthomatosis, chronic inflammatory demyelinating polyneuropathy (CIDP), Devic's syndrome, Diffuse myelinoclastic sclerosis, encephalomyelitis, Guillain-Barre syndrome, idiopathic inflammatory demyelinating disease (IIDD), Krabbe disease, Leber hereditary optic neuropathy, leukodystrophy, Marburg multiple sclerosis, Marchiafava-Bignami disease, metachromatic leukodystrophy (MLD), multifocal motor neuropathy (MMN), multiple sclerosis (MS), paraproteinemic demyelinating polyneuropathy, PelizaeusMerzbacher disease (PMD), progressive multifocal leukoencephaalopathy (PML), tropical spastic paraparesis (TSP), X-linked adrenoleukodystrophy (X-ALD, ALO, or X-linked ALO), or Zellweger syndrome.

Also provided are uses of the compound of Formula (I), or a pharmaceutically acceptable isomer, racemate, hydrate, solvate, isotope, or salt thereof thereof, in the manufacture of a medicament for the treatment of disease or condition in a subject, such as a human. Also provided are uses of the compound of Formula (II), or a pharmaceutically acceptable isomer, racemate, hydrate, solvate, isotope, or salt thereof thereof, in the manufacture of a medicament for the treatment of disease or condition in a subject, such as a human. In each of these uses the disease or condition may be selected from the group of acute disseminated encephalomyelitis (ADEM), acute hemorrhagic leukoencephalitis (AHL or AHLE), adult Refsum disease, infantile Refsum disease, Alexander disease, Alzheimer's disease, Balo concentric sclerosis, Canavan disease, central pontine myelinolysis (CPM), cerebral palsy, cerebrotendineous xanthomatosis, chronic inflammatory demyelinating polyneuropathy (CIDP), Devic's syndrome, Diffuse myelinoclastic sclerosis, encephalomyelitis, Guillain-Barre syndrome, idiopathic inflammatory demyelinating disease (IIDD), Krabbe disease, Leber hereditary optic neuropathy, leukodystrophy, Marburg multiple sclerosis, Marchiafava-Bignami disease, metachromatic leukodystrophy (MLD), multifocal motor neuropathy (MMN), multiple sclerosis (MS), paraproteinemic demyelinating polyneuropathy, PelizaeusMerzbacher disease (PMD), progressive multifocal leukoencephaalopathy (PML), tropical spastic paraparesis (TSP), X-linked adrenoleukodystrophy (X-ALD, ALO, or X-linked ALO), and Zellweger syndrome As used herein, the term "administration" refers to providing a compound, a prodrug of a compound, or a pharmaceutical composition comprising the compound or prodrug as described herein. The compound or composition can be administered by another person to the subject or it can be self-administered by the subject. Non-limiting examples of routes of administration are oral, parenteral (e.g., intravenous), or topical.

As used herein, the term "treatment" refers to an intervention that ameliorates a sign or symptom of a disease or pathological condition. As used herein, the terms "treatment", "treat" and "treating," with reference to a disease, pathological condition or symptom, also refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, a reduction in the number of relapses of the disease, an improvement in the overall health or well-being of the subject, or by other parameters well known in the art that are specific to the particular disease. A prophylactic treatment is a treatment administered to a subject who does not exhibit signs of a disease or exhibits only early signs, for the purpose of decreasing the risk of developing pathology. A therapeutic treatment is a treatment administered to a subject after signs and symptoms of the disease have developed.

As used herein, the term "subject" refers to an animal (e.g., a mammal, such as a human). A subject to be treated according to the methods described herein may be one who has been diagnosed with a neurodegenerative disease involving demyelination, insufficient myelination, or underdevelopment of a myelin sheath, e.g., a subject diagnosed with multiple sclerosis or cerebral palsy, or one at risk of developing the condition. Diagnosis may be performed by any method or technique known in the art. One skilled in the art will understand that a subject to be treated according to the present disclosure may have been subjected to standard tests or may have been identified, without examination, as one at risk due to the presence of one or more risk factors associated with the disease or condition.

As used herein, the term "effective amount" refers to a quantity of a specified agent sufficient to achieve a desired effect in a subject being treated with that agent. Ideally, an effective amount of an agent is an amount sufficient to inhibit or treat the disease without causing substantial toxicity in the subject. The effective amount of an agent will be dependent on the subject being treated, the severity of the affliction, and the manner of administration of the pharmaceutical composition. Methods of determining an effective amount of the disclosed compound sufficient to achieve a desired effect in a subject will be understood by those of skill in the art in light of this disclosure.

As used herein, the terms "acute disseminated encephalomyelitis" and "ADEM" refer to an immune-mediated demyelinating disease of the central nervous system. ADEM usually occurs following a viral infection, but may also appear following vaccination or following bacterial or parasitic infection. In some cases, ADEM develops spontaneously. The disease involves autoimmune demyelination, similar to multiple sclerosis, and is therefore considered a multiple sclerosis borderline disease. ADEM produces multiple inflammatory lesions in the brain and spinal cord, particularly in the white matter. The lesions are typically found in the subcortical and central white matter and cortical gray-white junction of both cerebral hemispheres, cerebellum, brainstem, and spinal cord, but periventricular white matter and gray matter of the cortex, thalami and basal ganglia may also be involved. When a patient suffers more than one demyelinating episode, the disease is referred to as recurrent disseminated encephalomyelitis or multiphasic disseminated encephalomyelitis.

As used herein, the terms "acute hemorrhagic leukoencephalitis," "AHL," and "AHLE" refer to a hyperacute and frequently fatal form of ADEM. This disease is also known as acute necrotizing encephalopathy (ANE), acute hemorrhagic encephalomyelitis (AHEM), acute necrotizing hemorrhagic leukoencephalitis (ANHLE), Weston-Hurst syndrome, or Hurst's disease.

As used herein, the term "adult Refsum disease" refers to an autosomal recessive neurological disease that is associated with the over-accumulation of phytanic acid in cells and tissues. Adult Refsum disease is divided into the adult Refsum disease 1 and adult Refsum disease 2 subtypes. Individuals with Refsum disease present with neurologic damage, cerebellar degeneration, and peripheral neuropathy. Onset is most commonly in childhood/adolescence with a progressive course, although periods of stagnation or remission occur. Symptoms also include ataxia, scaly skin (ichthyosis), difficulty hearing, and eye problems including cataracts and night blindness.

As used herein, the term "Alexander disease" refers to a very rare, congenital demyelinating disease. The disease primarily affects infants and children, causing developmental delay and changes in physical characteristics. Alexander disease is a type of leukodystrophy.

As used herein, the term "Alzheimer's disease" refers to the most common form of dementia. Symptoms of Alzheimer's disease include memory loss, confusion, irritability, aggression, mood swings and trouble with language. This disease is characterized by the loss of neurons and synapses in the cerebral cortex and certain subcortical regions. The loss results in gross atrophy of the affected regions, including degeneration in the temporal lobe, and parts of the frontal cortex and cingulate gyrus. Amyloid plaques and neurofibrillary tangles are visible by microscopy in brains of those afflicted with this disease. The cause of Alzheimer's disease is unknown; however, several hypotheses exist, including that the disease is caused by age-related myelin breakdown in the brain.

As used herein, the term "Balo concentric sclerosis" refers to a demyelinating disease similar to standard multiple sclerosis, but with the particularity that the demyelinated tissues form concentric layers. Patients with this disease can survive and/or have spontaneous remission. Typically, the clinical course is primary progressive, but a relapsing-remitting course has been reported.

As used herein, the term "Canavan disease" refers to an autosomal recessive degenerative disorder that causes progressive damage to nerve cells in the brain. Canavan disease is a leukodystrophy and is one of the most common degenerative cerebral diseases of infancy. This disease is also called Canavan-Van Bogaert-Bertrand disease, aspartoacylase deficiency and aminoacylase 2 deficiency.

As used herein, the terms "Central pontine myelinolysis" and "CPM" refer to a neurologic disease caused by severe damage of the myelin sheath of nerve cells in the brainstem, more precisely in the area termed the pons. The most common cause is the rapid correction of low blood sodium levels (hyponatremia). Frequently observed symptoms in this disorder are sudden para or quadraparesis, dysphagia, dysarthria, diplopia and loss of consciousness. The patient may experience locked-in syndrome where cognitive function is intact, but all muscles are paralyzed with the exception of eye blinking.

As used herein, the term "cerebral palsy" refers to a group of permanent, non-progressive movement disorders that cause physical disability. Cerebral palsy is caused by damage to the motor control centers of the developing brain and can occur during pregnancy, during childbirth, or after birth up to about age three. Patients with cerebral palsy exhibit damage to myelin sheaths.

As used herein, the term "cerebrotendineous xanthomatosis" refers to an inherited disorder associated with the deposition of a form of cholesterol (cholestanol) in the brain and other tissues and with elevated levels of cholesterol in plasma but with normal total cholesterol level. It is characterized by progressive cerebellar ataxia beginning after puberty and by juvenile cataracts, juvenile or infantile onset chronic diarrhea, childhood neurological deficit, and tendineous or tuberous xanthomas. This disorder is an autosomal recessive form of xanthomatosis. It falls within a group of genetic disorders called the leukodystrophies.

As used herein, the terms "chronic inflammatory demyelinating polyneuropathy" and "CIDP" refer to an acquired immune-mediated inflammatory disorder of the peripheral nervous system. The disorder is sometimes called chronic relapsing polyneuropathy (CRP) or chronic inflammatory demyelinating polyradiculoneuropathy (because it involves the nerve roots). CIDP is closely related to Guillain-Barré syndrome and it is considered the chronic counterpart of that acute disease. Its symptoms are also similar to progressive inflammatory neuropathy. An asymmetrical variant of CIDP is known as Lewis-Sumner syndrome. The pathologic hallmark of the disease is loss of the myelin sheath.

As used herein, the term "demyelinating disease" refers to any disease of the nervous system in which myelin is damaged or lost, or in which the growth or development of the myelin sheath is impaired. Demyelination inhibits the conduction of signals in the affected nerves, causing impairment in sensation, movement, cognition, or other functions for which nerves are involved. Demyelinating diseases have a number of different causes and can be hereditary or acquired. In some cases, a demyelinating disease is caused by an infectious agent, an autoimmune response, a toxic agent or traumatic injury. In other cases, the cause of the demyelinating disease is unknown ("idiopathic") or develops from a combination of factors.

As used herein, the term "Devic's syndrome" refers to an autoimmune, inflammatory disorder in which a person's immune system attacks the optic nerves and spinal cord, which results in inflammation of the optic nerve (optic neuritis) and the spinal cord (myelitis). Spinal cord lesions lead to varying degrees of weakness or paralysis in the legs or arms, loss of sensation, and/or bladder and bowel dysfunction. Although inflammation may also affect the brain, the lesions are different from those observed in MS. Devic's syndrome is similar to MS in that the body's immune system attacks the myelin surrounding nerve cells. Unlike standard MS, the attacks are not believed to be mediated by the immune system's T cells but rather by antibodies called NMO-IgG. These antibodies target a protein called aquaporin 4 in the cell membranes of astrocytes which acts as a channel for the transport of water across the cell membrane. Devic's syndrome is also known as Devic's syndrome or neuromyelitis optica (NMO).

As used herein, the term "diffuse myelinoclastic sclerosis" refers to an uncommon neurodegenerative disease that presents clinically as pseudotumoral demyelinating lesions. It usually begins in childhood, affecting children between 5 and 14 years old; however, cases in adults are possible. This disease is considered one of the borderline forms of MS and is sometimes referred to as Schilder's disease.

As used herein, the term "encephalomyelitis" refers to inflammation of the brain and spinal cord.

As used herein, the term "Guillain-Barré syndrome" refers to an acute polyneuropathy, a disorder affecting the peripheral nervous system. Ascending paralysis, weakness beginning in the feet and hands and migrating towards the trunk, is the most typical symptom, and some subtypes cause change in sensation or pain, as well as dysfunction of the autonomic nervous system. It can cause life-threatening complications, in particular if the respiratory muscles are affected or if the autonomic nervous system is involved. This disease is usually triggered by an infection. Acute inflammatory demyelinating polyneuropathy (AIDP) is the most common subtype of this disease. Other subtypes of Guillain-Barré syndrome include Miller Fischer syndrome, acute motor axonal neuropathy (Chinese paralytic syndrome), acute motor sensory axonal neuropathy, acute panautonomic neuropathy, and Bickerstaff's brainstem encephalitis.

As used herein, the terms "idiopathic inflammatory demyelinating disease" and "IIDD" refer to a broad spectrum of central nervous system disorders that can usually be differentiated on the basis of clinical, imaging, laboratory and pathological findings. Idiopathic inflammatory demyelinating diseases are sometimes known as borderline forms of multiple sclerosis. IIDD generally refers to a collection of multiple sclerosis variant diseases, including but not limited to, optic-spinal MS, Devic's disease, ADEM, acute hemorrhagic leukoencephalitis, Balo concentric sclerosis, Schilder disease, Marburg multiple sclerosis, tumefactive multiple sclerosis and solitary sclerosis.

As used herein, the term "infantile Refsum disease" refers to a peroxisome biogenesis disorder associated with deficiencies in the catabolism of very long chain fatty acids and branched chain fatty acids (such as phytanic acid) and plasmalogen biosynthesis. Infantile Refsum disease is a rare, autosomal recessive congenital disorder, and one of three peroxisome biogenesis disorders that belong to the Zellweger spectrum of peroxisome biogenesis disorders.

As used herein, the term "Krabbe disease" refers to a rare, often fatal degenerative disorder that affects the myelin sheath of the nervous system. It is a form of sphingolipidosis, as it involves dysfunctional metabolism of sphingolipids. This condition is inherited in an autosomal recessive pattern. Krabbe disease is also known as globoid cell leukodystrophy or galactosylceramide lipidosis.

As used herein, the term "Leber hereditary optic neuropathy" refers to a mitochondrially inherited (transmitted from mother to offspring) degeneration of retinal ganglion cells (RGCs) and their axons that leads to an acute or subacute loss of central vision; this affects predominantly young adult males.

As used herein, the term "leukodystrophy" refers to a group of diseases that affects the growth or development of the myelin sheath.

As used herein, the term "leukoencephalopathy" refers to any of a group of diseases affecting the white substance of the brain; can refer specifically to several diseases including, for example, "leukoencephalopathy with vanishing white matter" and "toxic leukoencephalopathy." Leukoencephalopathies are leukodystrophy-like diseases.

As used herein, the term "Marburg multiple sclerosis" refers to a condition in which the central nervous system has multiple demyelinating lesions with atypical characteristics for those of standard multiple sclerosis. This disease is a borderline form of multiple sclerosis and is also known as tumefactive multiple sclerosis or fulminant multiple sclerosis. It is called tumefactive because the lesions are "tumor-like" and they mimic tumors clinically, radiologically and sometimes pathologically.

As used herein, the term "Marchiafava-Bignami disease" refers to a progressive neurological disease characterized by corpus callosum demyelination and necrosis and subsequent atrophy. It is classically associated with chronic alcoholics.

As used herein, the terms "metachromatic leukodystrophy" and "MLD" refer to a lysosomal storage disease that is commonly listed in the family of leukodystrophies, as well as in the sphingolipidoses as it affects the metabolism of sphingolipids. MLD is directly caused by a deficiency of the enzyme arylsulfatase A.

As used herein, the terms "multifocal motor neuropathy" and "MMN" refer to a progressively worsening condition where muscles in the extremities gradually weaken. This disorder, a motor neuropathy syndrome, is sometimes mistaken for amyotrophic lateral sclerosis (ALS) because of the similarity in the clinical picture, especially if muscle fasciculations are present. MMN is usually asymmetric and is thought to be autoimmune.

As used herein, the terms "multiple sclerosis" and "MS" refer to a slowly progressive CNS disease characterized by disseminated patches of demyelination in the brain and spinal cord, resulting in multiple and varied neurological symptoms and signs, usually with remissions and exacerbation. The cause of MS is unknown but an immunological abnormality is suspected. An increased family incidence suggests genetic susceptibility, and women are somewhat more often affected than men. The symptoms of MS include weakness, lack of coordination, paresthesias, speech disturbances, and visual disturbances, most commonly double vision. More specific signs and symptoms depend on the location of the lesions and the severity and destructiveness of the inflammatory and sclerotic processes. Relapsing-remitting multiple sclerosis (RRMS) is a clinical course of MS that is characterized by clearly defined, acute attacks with full or partial recovery and no disease progression between attacks. Secondary-progressive multiple sclerosis (SPMS) is a clinical course of MS that initially is relapsing-remitting, and then becomes progressive at a variable rate, possibly with an occasional relapse and minor remission. Primary-progressive multiple sclerosis (PPMS) presents initially in the progressive form. A clinically isolated syndrome is the first neurologic episode, which is caused by inflammation/demyelination at one or more sites in the CNS. Progressive-relapsing multiple sclerosis (PRMS) is a rare form of MS (~5%) characterized by a steadily worsening disease state from onset, with acute relapses but no remissions.

As used herein, the term "myelin" refers to a lipid substance forming a sheath (known as the myelin sheath) around the axons of certain nerve fibers. Myelin is an electrical insulator that serves to speed the conduction of nerve impulses in nerve fibers. "Myelination" (also "myelinization") refers to the development or formation of a myelin sheath around a nerve fiber. Similarly, "remyelination" (also, "remyelinization") refers to the repair or reformation of the myelin sheath, such as following injury, exposure to a toxic agent, or an inflammatory response, or during the course of a demyelinating disease.

As used herein, the term "neurodegenerative disease" refers to any type of disease that is characterized by the progressive deterioration of the nervous system.

As used herein, the term "neuropathy" refers to a functional disturbance or pathological change in the peripheral nervous system. Axonal neuropathy refers to a disorder disrupting the normal functioning of the axons.

As used herein, the term "paraproteinemic demyelinating polyneuropathy" refers to a type of peripheral neuropathy characterized by auto antibodies directed against myelin associated glycoproteins (MAG). Anti-MAG antibodies inhibit the production of myelin, thereby leading to neuropathy.

As used herein, the terms "Pelizaeus-Merzbacher disease" and "PMD" refer to a rare central nervous system disorder in which coordination, motor abilities, and intellectual function are delayed to variable extents. The disease is one in a group of genetic disorders collectively known as leukodystrophies.

As used herein, the terms "peroneal muscular atrophy" and "PMA" refer to a genetically and clinically heterogeneous group of inherited disorders of the peripheral nervous system characterized by progressive loss of muscle tissue and touch sensation across various parts of the body. This disease is also known as Charcot-Marie-Tooth disease (CMT), Charcot-Marie-Tooth neuropathy and hereditary motor and sensory neuropathy (HMSN).

As used herein, the terms "progressive multifocal leukoencephalopathy" and "PML" refer to rare and usually fatal viral disease that is characterized by progressive damage or inflammation of the white matter of the brain in multiple locations. PML occurs almost exclusively in people with severe immune deficiency. The cause of PML is a type of polyomavirus called the JC virus. The virus is widespread, with 86% of the general population presenting antibodies, but it usually remains latent, causing disease only when the immune system has been severely weakened. PML is a demyelinating disease, in which the myelin sheath covering the axons of nerve cells is gradually destroyed, impairing the transmission of nerve impulses. The disease may occur in subjects (e.g., humans) with severe immune deficiency, such as transplant patients on immunosuppressive medications or those receiving certain kinds of medications. For example, PML has been associated with administration of rituximab (off-label use in the treatment of multiple sclerosis). It affects the white matter, which is mostly composed of axons from the outermost parts of the brain (cortex). Symptoms include weakness or paralysis, vision loss, impaired speech, and cognitive deterioration.

As used herein, the term "sobetirome" refers to a synthetic diarylmethane derivative that was investigated clinically as a potential therapeutic for hypercholesterolemia (see U.S. Pat. No. 5,883,294, which is incorporated by reference herein). Other names for sobetirome found in the literature and regulatory filings include QRX-431 and GC-1.

As used herein, the term "transverse myelitis" refers to a neurological disorder caused by an inflammatory process of the grey and white matter of the spinal cord, leading to axonal demyelination. Demyelination arises idiopathically following infections or vaccination, or due to multiple sclerosis. Symptoms include weakness and numbness of the limbs as well as motor, sensory, and sphincter deficits. Severe back pain may occur in some patients at the onset of the disease.

As used herein, the terms "tropical spastic paraparesis" and "TSP" refer to an infection of the spinal cord by human T-lymphotropic virus resulting in paraparesis, weakness of the legs. TSP is also known as HTLV associated myelopathy or chronic progressive myelopathy. As the name suggests, this disease is most common in tropical regions, including the Caribbean and Africa.

As used herein, the term "Van der Knaap disease" refers to a form of hereditary CNS demyelinating disease. This disease is a type of leukodystrophy and is also known as megalencephalic leukoencephalopathy with subcortical cysts (MLC).

As used herein, the terms "X-linked adrenoleukodystrophy," "X-ALD," "ALD," and "X-linked ALD" refer to a rare, inherited metabolic disorder that leads to progressive brain damage, mental deterioration, failure of the adrenal glands, muscle spasms, blindness and eventually death. ALD is one disease in a group of inherited disorders called leukodystrophies. Adrenoleukodystrophy progressively damages myelin. X-linked ALD male patients may be divided into 7 phenotypes: childhood cerebral (progressive neurodegenerative decline leading to a vegetative state), adolescent (similar to childhood cerebral form but with a slower progression), adrenomyeloneuropathy (progressive neuropathy, paraparesis, may progress to cerebral involvement), adult cerebral (dementia, similar progression to childhood cerebral form), olivo-ponto-cerebellar (cerebral and brain stem involvement), Addison disease (adrenal insufficiency), asymptomatic (no clinical presentation, subclinical adrenal insufficiency, or AMN phenotype). X-linked ALD female patients may be divided into 5 phenotypes: asymptomatic (no neurologic or adrenal involvement), mild myelopathy, moderate to severe myelopathy (similar to male AMN phenotype), cerebral (progressive dementia and decline), and adrenal (primary adrenal insufficiency). X-linked ALD patients may progress from one phenotype to another over the course of their life. ALD is also known as Addison-Schilder disease or Siemerling-Creutzfeldt disease.

As used herein, the term "Zellweger syndrome" refers to a rare congenital disorder, characterized by the reduction or absence of functional peroxisomes in the cells of an individual. This disease is classified as a leukodystrophy and is one of three peroxisome biogenesis disorders that belong to the Zellweger spectrum of peroxisome biogenesis disorders.

Compounds having the structure of Formula (I) or Formula (II) can be synthesized using standard synthetic techniques known to those of skill in the art. For example, compounds of the present invention can be synthesized using appropriately modified synthetic procedures set forth in Scheme 1.

To this end, the reactions, processes, and synthetic methods described herein are not limited to the specific conditions described in the following experimental section, but rather are intended as a guide to one with suitable skill in this field. For example, reactions may be carried out in any suitable solvent, or other reagents to perform the transformation[s] necessary. Generally, suitable solvents are protic or aprotic solvents which are substantially non-reactive with the reactants, the intermediates or products at the temperatures at which the reactions are carried out (i.e., temperatures which may range from the freezing to boiling temperatures). A given reaction may be carried out in one solvent or a mixture of more than one solvent. Depending on the particular reaction, suitable solvents for a particular work-up following the reaction may be employed.

4-hydroxy-2,6-dihalobenzaldehyde intermediates are produced by selective deprotonation of the 4-position of trimethylsilyl ether protected 3,5-dihalophenols with lithium amide reagents. These intermediates were used in a slightly altered version of the sobetirome synthesis reported in Placzek A T and Scanlan T S, Tetrahedron 71, 5946-5951 (2015); which is incorporated by reference herein. The 4-hydroxy-2,6-dihalobenzaldehyde intermediates could not be alkylated with tertbutyl chloroacetate using the standard cesium carbonate/DMF conditions due to the halogen substitutions reducing the nucleophilicity of the phenol. However, the reaction went to completion and in good yield after converting the alkyl chloride into an alkyl iodide via an in situ Finklestein reaction.

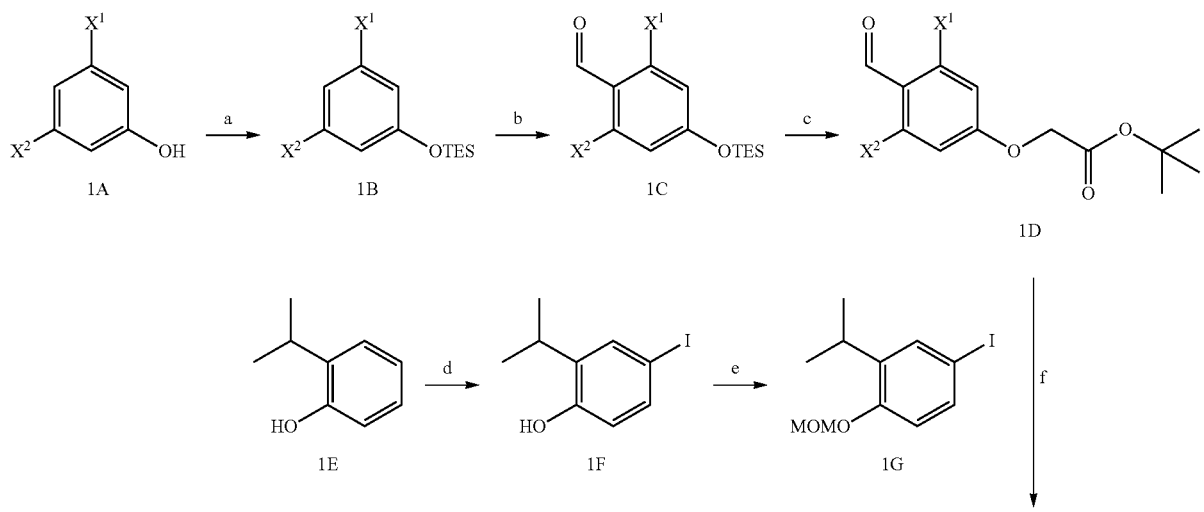

Scheme 1

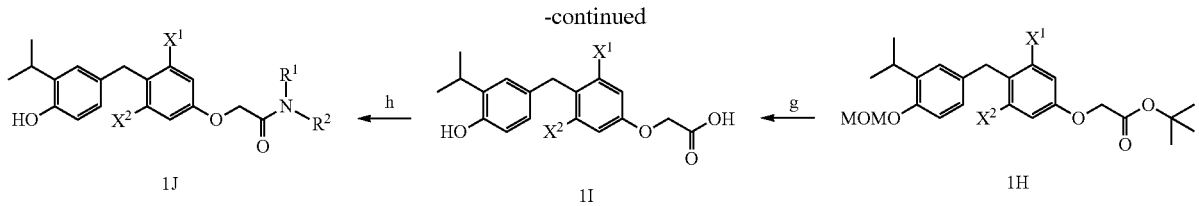

Reagents and Conditions: (a) triethylsilyl chloride, imidazole, DCM, 0° C., 95%; (b) (i) nBuLi, DIA/TMP, THF, -78° C. (ii) DMF, 56-67%; (c) tertchloroacetate, NaI, Cs2CO3, acetone, 60-65° C., 84-88%; (d) NaI, NaOH, NaOCl, MeOH, H₂O, 87% (e) MOMCl, TBAI, NaOH, DCM, H2O, 81%; (f) (i) iPMgCl, THF, 0° C. to RT (ii) 4, -78° C., 54-79%; (g) TFA, triethylsilane, DCM, 0° C. to RT, 58-69%; (h) MeOH, H₂SO₄, NHR¹R², 65° C. to RT.

After forming the tert-butyl oxyacetate intermediate, the carbon-carbon bond formation proceeded in the same fashion as with sobetirome by forming an arylmagnesium with 1G that attacked the benzaldehyde to form a carbinol intermediate. The arylmagnesium nucleophile will not likely exchange with aryl chlorides or bromides at cryogenic temperatures and is compatible with the tert-butyl ester protecting group. Reduction of the carbinol and deprotection of the tert-butyl ester and methoxymethyl ether protecting groups proceeded simultaneously with TFA and triethylsilane in dichloromethane.

EXAMPLES

The invention is further illustrated by the following examples. The examples below are non-limiting are merely representative of various aspects of the invention. Solid and dotted wedges within the structures herein disclosed illustrate relative stereochemistry, with absolute stereochemistry depicted only when specifically stated or delineated.

PREPARATION OF INTERMEDIATES

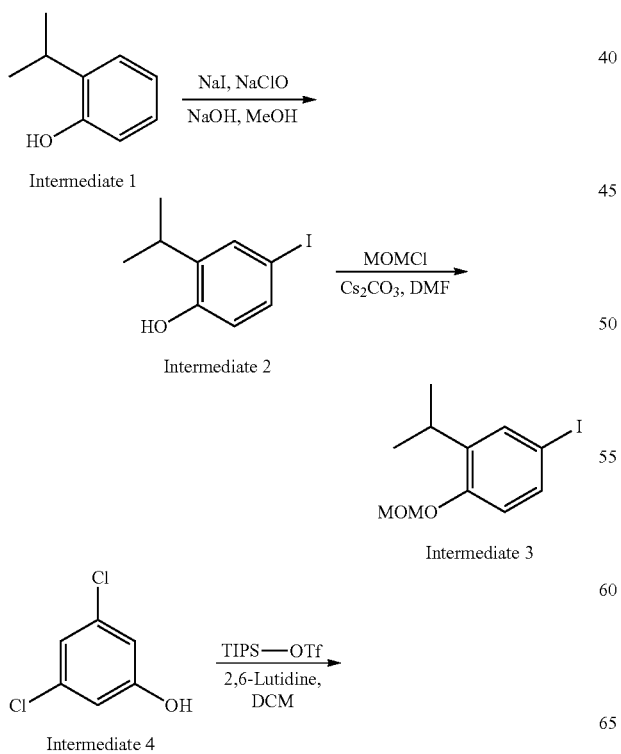

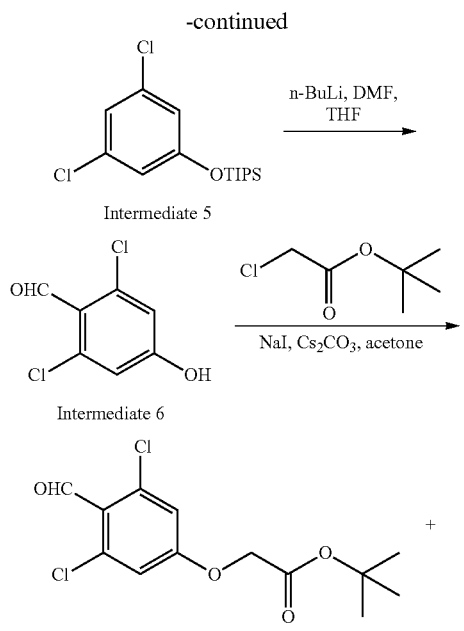

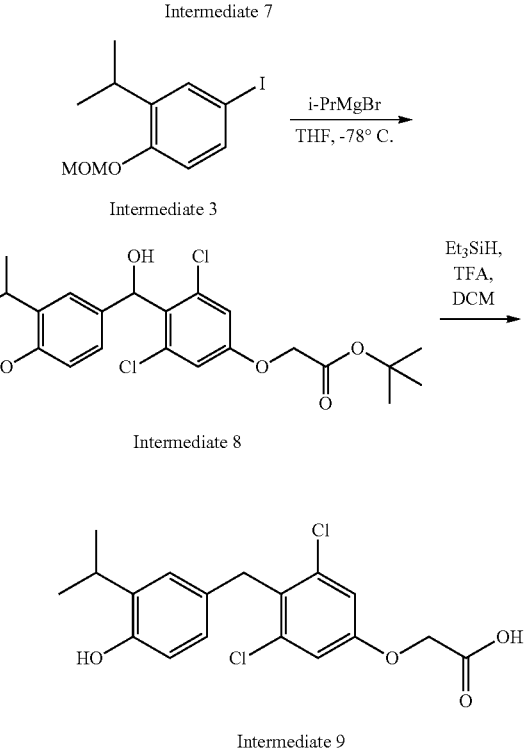

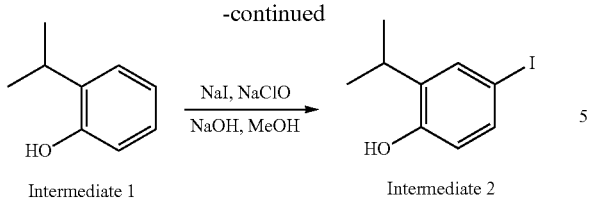

Intermediate 1    Intermediate 2

To a solution of 2-isopropylphenol (Intermediate 1) (840 g, 6.17 mol, 1.0 eq) in methanol (10 L) was added NaI (924.5 g, 6.17 mol, 1.0 eq) and NaOH (246.7 g, 6.17 mol, 1.0 eq). The mixture was cooled to −10° C. and sodium hypochlorite (9.6 L, 6.17 mol, 15% in water) was added dropwise over 4 h. The mixture was quenched by slowly adding 10% aq $Na_2S_2O_3$ (5 L) and the mixture was acidified with concentrated hydrochoric acid. The mixture was extracted with EtOAc (5 L*2). The combined organic phase was washed with brine (5 L), dried over $Na_2SO_4$, concentrated in vacuum. The residue was purified by silica column (pet. ether/EtOAc=100/1 to 20/1) to afford 4-iodo-2-isopropyl-phenol (Intermediate 2) (800 g, 49% yield) as a reddish oil. $^1$H NMR (400 MHz, DMSO-$d_6$) δ 10.08 (s, 1H), 7.85 (d, J=2.3 Hz, 1H), 7.80 (dd, J=8.4, 2.3 Hz, 1H), 7.13 (d, J=8.4 Hz, 1H), 3.64 (m, 1H), 1.64 (d, J=6.9 Hz, 6H).

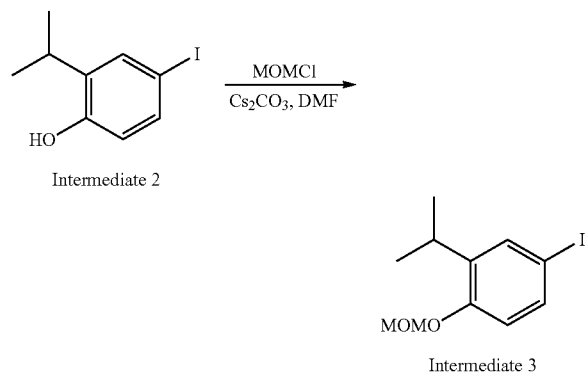

Intermediate 2

Intermediate 3

To a solution of Intermediate 2 (283 g, 1.08 mol, 1.0 eq) in DMF (3.28 L) was added MOMCl (258.4 g, 3.24 mol, 3.0 eq) and $Cs_2CO_3$ (1.05 kg, 3.24 mol, 3.0 eq). The mixture was stirred at rt for three hours under $N_2$ atmosphere. The mixture was diluted with water (10 L) and extracted with EtOAc (5 L×2). The combined organic layers were dried over $Na_2SO_4$ and concentrated under reduced pressure. The residue was purified by silica column (pet. ether/EtOAc=100/1 to 30/1) to afford 4-iodo-2-isopropyl-1-(methoxymethoxy)benzene (Intermediate 3) (250 g, 76% yield) as a red oil. $^1$H NMR (400 MHz, DMSO-$d_6$) δ7.45 (d, J=8.0 Hz, 2H), 6.87 (d, J=8.0 Hz, 1H), 5.20 (s, 2H), 3.37 (s, 3H), 3.26-3.18 (m, 1H), 1.14 (d, J=8.0 Hz, 6H).

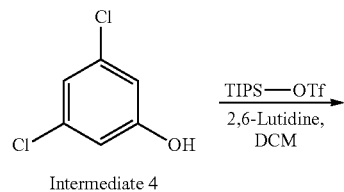

Intermediate 4

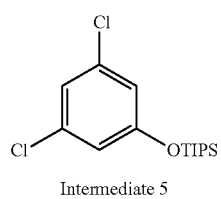

Intermediate 5

To a solution of 3,5-dichlorophenol (Intermediate 4) (70 g, 0.43 mol, 1.0 eq) in DCM (0.9 L) was added 2,6-lutidine (115.0 g, 1.07 mol, 2.5 eq). The solution was cooled to 0° C. TIPS-OTf (171.1 g, 0.56 mol, 1.3 eq) was added dropwise. The mixture was stirred at 0° C. for 2 h. The mixture was concentrated in vacuum. Petroleum ether (500 mL) was added, the resulting solution was washed with water (200 mL*3), and brine (200 mL), then dried over $Na_2SO_4$, and concentrated in vacuum to give the crude (3,5-dichlorophenoxy)-triisopropylsilane (Intermediate 5) (137 g, quantitative yield) as a yellow oil. This crude product was used for the next step without further purification.

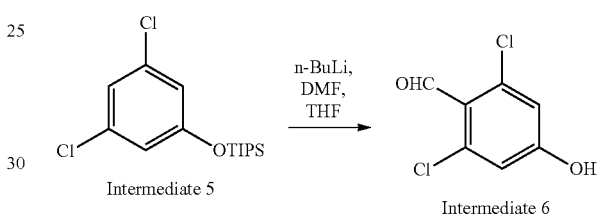

Intermediate 5

Intermediate 6

To a solution of Intermediate 5 (310 g, 0.98 mol, 1.0 eq) in THF (1.3 L) at −75° C. was dropwise added n-BuLi (0.44 L, 1.1 mol, 1.1 eq, 2.3 M in THF). This mixture was stirred at −70° C. for 50 min. Anhydrous DMF (106.4 g, 1.5 mol, 1.5 eq) was added dropwise, keeping the reaction temperature below −65° C. The reaction mixture was stirred at −65° C. for 3 h. The mixture was quenched with aqueous saturated $NH_4Cl$ (500 mL) and acidified with 6N HCl. The mixture was extracted with EtOAc (1000 mL*2). The combined EtOAc phase was washed with brine (500 mL), dried over $Na_2SO_4$, and concentrated in vacuum to afford 2,6-dichloro-4-hydroxy-benzaldehyde (Intermediate 6) (90 g, 49% yield) as a yellow solid. $^1$H NMR (400 MHz, DMSO-$d_6$) δ 11.44 (s, 1H), 10.24 (s, 1H), 6.93 (s, 2H).

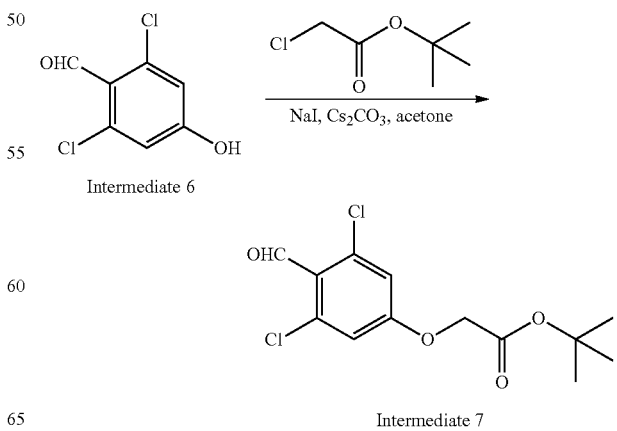

Intermediate 6

Intermediate 7

To a solution of Intermediate 6 (176.0 g, 0.92 mol, 1.0 eq) in acetone (3.2 L) was added NaI (276.2 g, 1.84 mol, 2.0 eq) and Cs$_2$CO$_3$ (300 g, 0.92 mol, 1.0 eq). Tert-butyl 2-chloroacetate (277.53 g, 1.84 mol, 2.0 eq) was added dropwise. The mixture was heated to reflux for 2 h. The mixture was filtered. The filtrate was diluted with water (1 L), extracted with EtOAc (1 L*2). The combined EtOAc phase was washed with brine (1 L), dried over Na$_2$SO$_4$, and concentrated in vacuum. The residue was purified by silica gel chromatography (pet. ether:EtOAc=50:1 to 20:1) to afford tert-butyl 2-(3,5-dichloro-4-formyl-phenoxy)acetate (Intermediate 7) (210 g, 75% yield) as a light yellow solid. $^1$H NMR (400 MHz, DMSO-d$_6$) δ 10.27 (s, 1H), 7.21 (s, 2H), 4.90 (s, 2H), 1.42 (s, 9H).

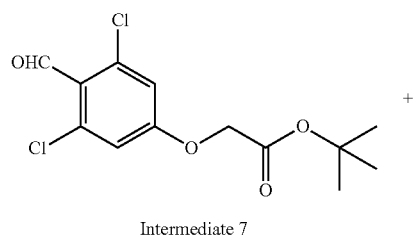

Intermediate 7

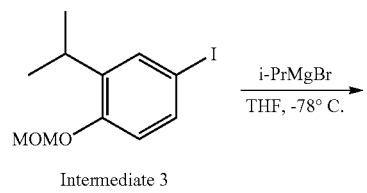

Intermediate 3

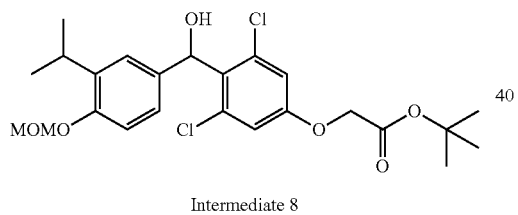

Intermediate 8

A solution of Intermediate 3 (130 g, 0.42 mol, 1.29 eq) in THF (2.4 L) was cooled to −20° C. i-PrMgCl (0.66 mol, 330 mL, 2.0 eq, 2M in THF) was added dropwise. The mixture was stirred at rt for 2 h. The mixture was cooled down to −68° C. and Intermediate 7 (100.5 g, 0.33 mol, 1.0 eq) in THF (300 mL) was added dropwise. The solution was stirred at −68° C. for 2.5 h. The mixture was quenched with aqueous saturated NH$_4$Cl (500 mL), then water (1 L). The mixture was extracted with EtOAc (1.2 L*2). The combined EtOAc phase was washed with brine (500 mL), dried over Na$_2$SO$_4$ and concentrated under reduced pressure. The residue was purified by silica gel chromatography (pet. ether:EtOAc=100:1 to 20:1) to afford tert-butyl 2-[3,5-dichloro-4-[hydroxy-[3-isopropyl-4-(methoxymethoxy)phenyl]-methyl]phenoxy]acetate (Intermediate 8) (98 g, 61% yield) as a yellow oil. $^1$H NMR (400 MHz, Chloroform-d) δ 7.23 (d, J=2.3 Hz, 1H), 6.97 (d, J=8.5 Hz, 1H), 6.96 (dd, J=2.4, 8.5 Hz, 1H), 6.90 (s, 2H), 6.48 (s, 1H), 5.18 (s, 2H), 4.88 (s, 1H), 4.51 (s, 2H), 3.48 (s, 3H), 3.35-3.28 (m, 1H), 1.50 (s, 9H), 1.18 (d, J=6.7 Hz, 6H).

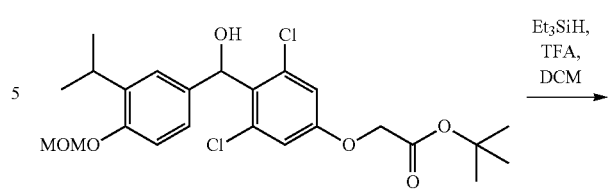

Intermediate 8

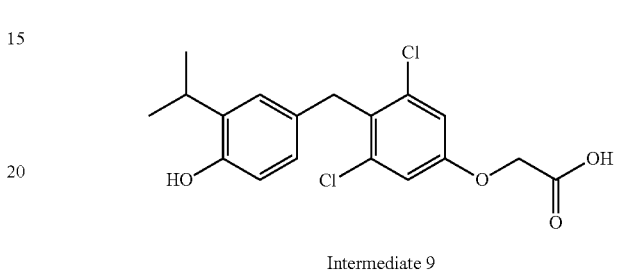

Intermediate 9

To a solution of Intermediate 8 in DCM (1 L) at 0° C. was added Et$_3$SiH (0.5 mol, 85 mL, 5.0 eq). TFA (352.4 g, 3.0 mol, 30.0 eq) in DCM (150 mL) was added dropwise. The mixture was stirred at 0° C. for 10 min and was stirred at rt for 4 h. The mixture was evaporated under reduced pressure. Hexane (200 mL) was added to the residue and the mixture stirred for 20 min. The mixture was filtered and washed with pet. ether:EtOAc=10:1 to afford crude Intermediate 9 (26 g, 69% yield, 85% purity). $^1$H NMR (400 MHz, DMSO-d$_6$) δ 13.15 (s, 1H), 9.08 (s, 1H), 7.10 (s, 2H), 6.97 (d, J=2.1 Hz, 1H), 6.72-6.55 (m, 2H), 4.76 (s, 2H), 4.03 (s, 2H), 3.17-3.08 (m, 1H), 1.10 (d, J=6.9 Hz, 6H).

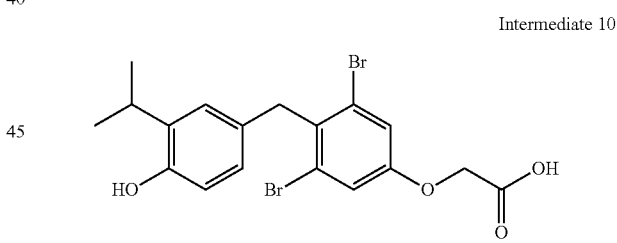

Intermediate 10

Intermediate 10 was prepared according to the procedures described above, substituting 3,5-dibromophenol for 3,5-dichlorophenol in Step 3.

By the same procedures, the corresponding intermediate having "mixed" halogen substituents may be made in the same manner; namely, a chlorine and a bromine in place of two chlorines or two bromines as shown above in Intermediates 9 and 10, respectively. Such a mixed intermediate may be prepared according to the procedures described above, substituting 3-chloro-5-bromophenol for 3,5-dichlorophenol in Step 3. While the following examples illustrate synthesis of compounds having two chloro or two brome substituents (employing Intermediates 9 and 10 in their synthesis), the corresponding "mixed" compounds may be made in the same manner by employing such a "mixed" intermediate.

Example 1

(Compound 2)

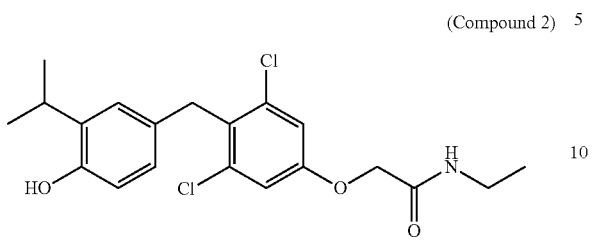

To a solution of Intermediate 9 (250 mg) in THF (10 mL) were added ethylamine (3 eq), EDCI, HOBt, and diisopropylamine (1.5 eq each). The reaction was stirred overnight at room temperature. The mixture was diluted with water (10 mL), extracted with EtOAc (10 mL*3). The combined EtOAc phase was washed by brine (10 mL), dried over Na$_2$SO$_4$, concentrated under reduce pressure and purified by prep-HPLC (ACN/water range from 30/70 to 85/15) to afford the titled compound as white solid. MS(ES-API) m/z 396.0/398.0.

Example 2

(Compound 5)

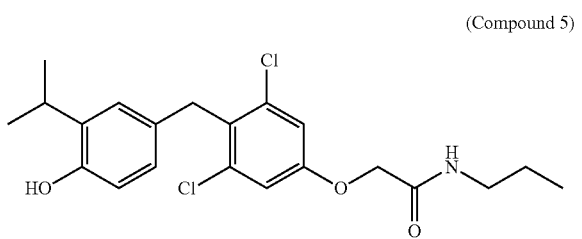

The titled compound was prepared according to the procedure of Example 1, substituting n-propylamine for ethylamine. MS(ES-API) m/z 410.0/412.0.

Example 3

(Compound 8)

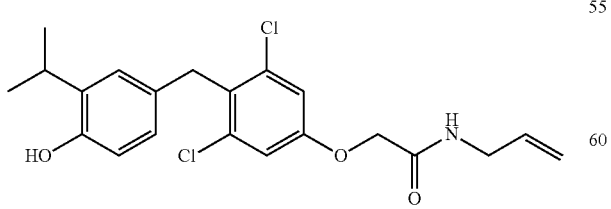

The titled compound was prepared according to the procedure of Example 1, substituting allylamine for ethylamine. MS(ES-API) m/z 408.0/410.0.

Example 4

(Compound 11)

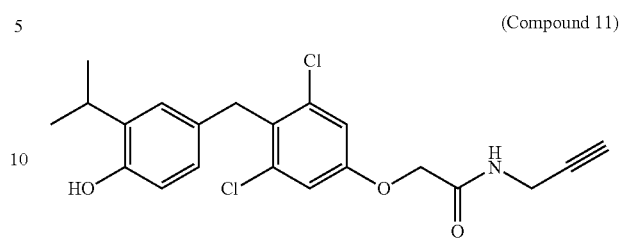

The titled compound was prepared according to the procedure of Example 1, substituting propargylamine for ethylamine. MS(ES-API) m/z 406.0/408.0.

Example 5

(Compound 14)

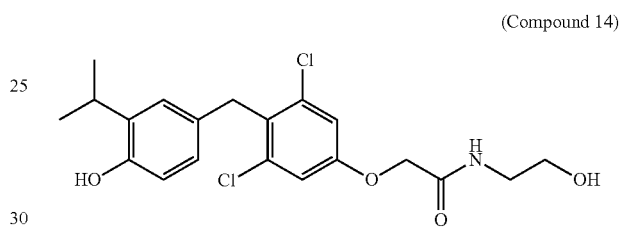

The titled compound was prepared according to the procedure of Example 1, substituting 2-aminoethanol for ethylamine. MS(ES-API) m/z 412.0/413.9.

Example 6

(Compound 20-R)

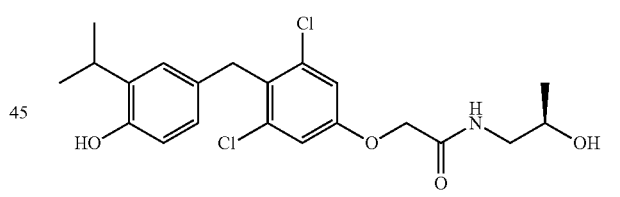

The titled compound was prepared according to the procedure of Example 1, substituting (R)-(−)-1-amino-2-propanol for ethylamine. MS(ES-API) m/z 426.0/428.0.

Example 7

(Compound 20-S)

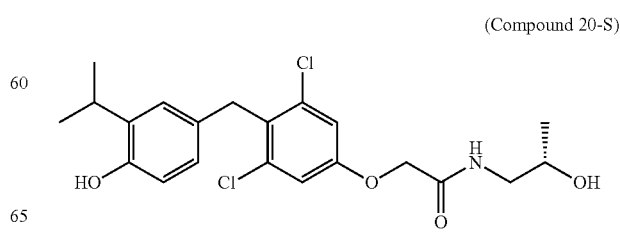

The titled compound was prepared according to the procedure of Example 1, substituting (S)-(+)-1-amino-2-propanol for ethylamine. MS(ES-API) m/z 426.0/428.0.

Example 8

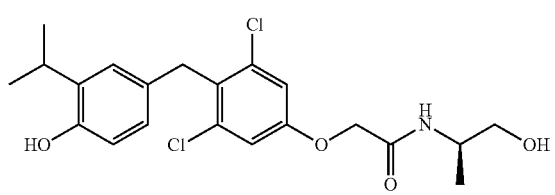
(Compound 17-R)

The titled compound was prepared according to the procedure of Example 1, substituting (R)-(−)-2-amino-1-propanol for ethylamine. MS(ES-API) m/z 424.1/426.0.

Example 9

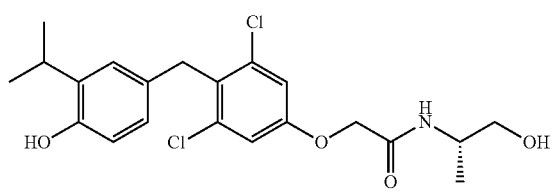
(Compound 17-S)

The titled compound was prepared according to the procedure of Example 1, substituting (S)-(+)-2-amino-1-propanol for ethylamine. MS(ES-API) m/z 426.0/428.1.

Example 10

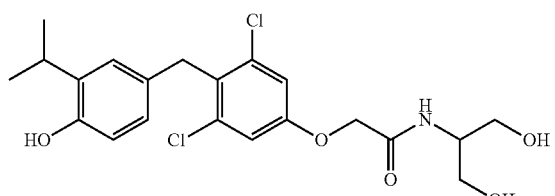
(Compound 23)

The titled compound was prepared according to the procedure of Example 1, substituting 2-amino-1,3-propanediol for ethylamine. MS(ES-API) m/z 442.0/444.0.

Example 11

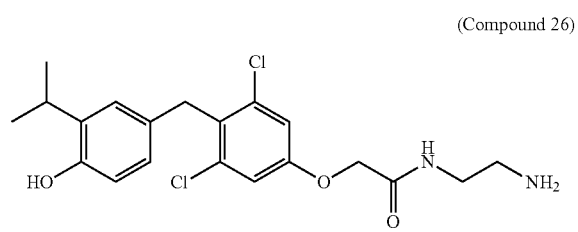
(Compound 26)

The titled compound was prepared according to the procedure of Example 1, substituting ethylenediamine for ethylamine. MS(ES-API) m/z 411.0/413.0.

Example 12

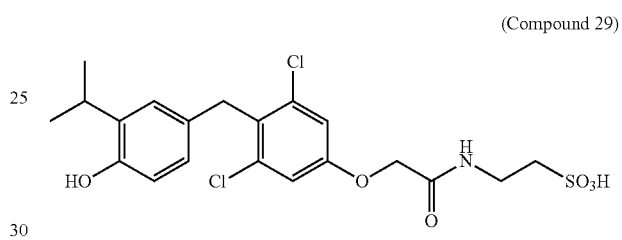
(Compound 29)

The titled compound was prepared according to the procedure of Example 1, substituting 2-aminoethanesulfonic acid for ethylamine. MS(ES-API) m/z 474.0/475.9.

Example 13

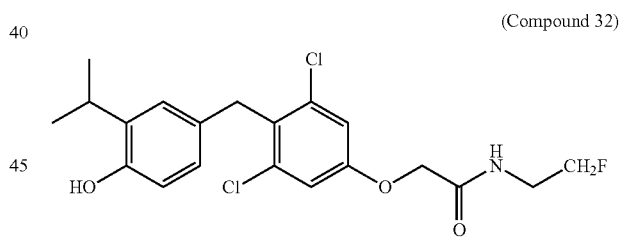
(Compound 32)

The titled compound was prepared according to the procedure of Example 1, substituting 2-fluoroethylamine for ethylamine. MS(ES-API) m/z 414.0/416.0.

Example 14

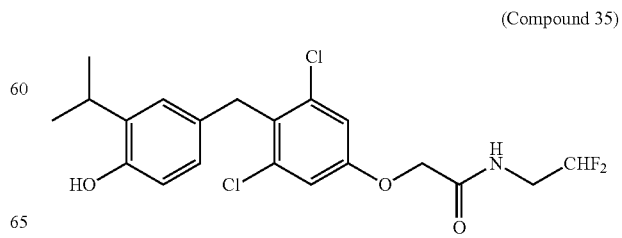
(Compound 35)

The titled compound was prepared according to the procedure of Example 1, substituting 2,2-difluoroethylamine for ethylamine. MS(ES-API) m/z 432.0/434.0.

Example 15

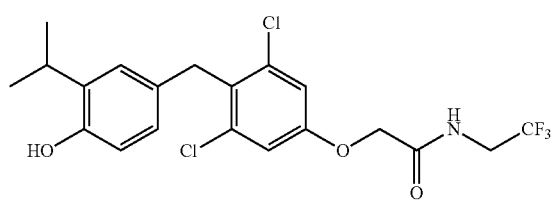
(Compound 38)

The titled compound was prepared according to the procedure of Example 1, substituting 2,2,2-trifluoroethylamine for ethylamine. MS(ES-API) m/z 448.0/449.9.

Example 16

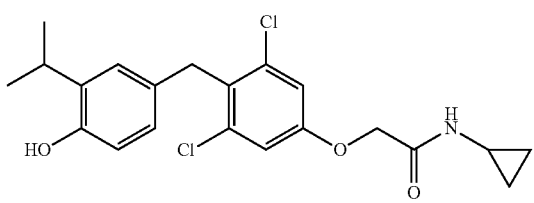
(Compound 41)

The titled compound was prepared according to the procedure of Example 1, substituting cyclopropylamine for ethylamine. MS(ES-API) m/z 406.0/408.1.

Example 17

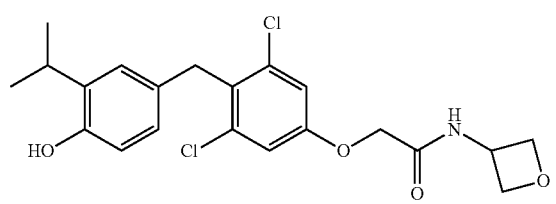
(Compound 44)

The titled compound was prepared according to the procedure of Example 1, substituting 3-aminooxetane for ethylamine. MS(ES-API) m/z 422.0/423.9.

Example 18

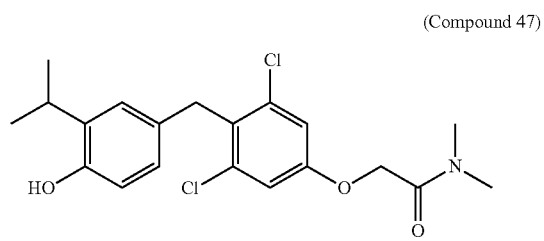
(Compound 47)

The titled compound was prepared according to the procedure of Example 1, substituting dimethylamine for ethylamine. MS(ES-API) m/z 394.0/395.9.

Example 19

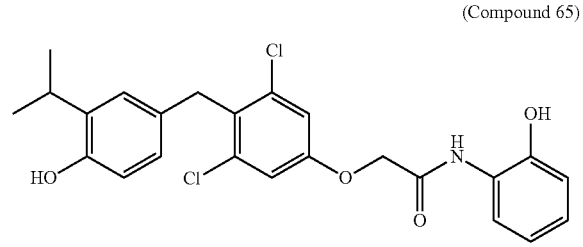
(Compound 65)

The titled compound was prepared according to the procedure of Example 1, substituting 2-hydroxyaniline for ethylamine. MS(ES-API) m/z 457.8/460.0.

Example 20

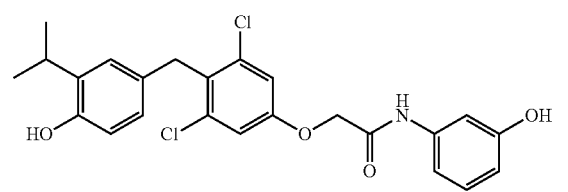
(Compound 68)

The titled compound was prepared according to the procedure of Example 1, substituting 3-hydroxyaniline for ethylamine. MS(ES-API) m/z 458.0/460.0.

Example 21

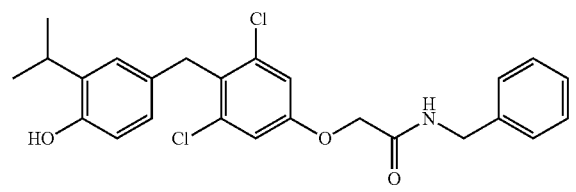 [SMILES: CC(C)c1cc(Cc2c(Br)cc(OCC(=O)NCc3ccccc3)cc2Br)ccc1O]
(Compound 74)

The titled compound was prepared according to the procedure of Example 1, substituting benzylamine for ethylamine. MS(ES-API) m/z 458.0/460.0.

Example 22

(Compound 77)

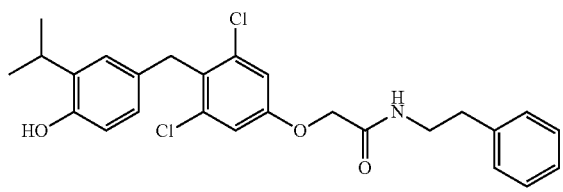 [SMILES: CC(C)c1cc(Cc2c(Cl)cc(OCC(=O)NCCc3ccccc3)cc2Br)ccc1O]

The titled compound was prepared according to the procedure of Example 1, substituting 2-phenethylamine for ethylamine. MS(ES-API) m/z 470.0/472.1.

Example 23

(Compound 80)

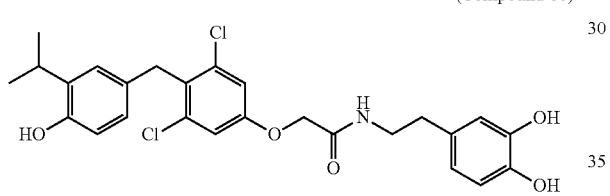

The titled compound was prepared according to the procedure of Example 1, substituting 2-(3,4-dihydroxy) phenethylamine for ethylamine. MS(ES-API) m/z 502.1/504.0.

Example 24

(Compound 71)

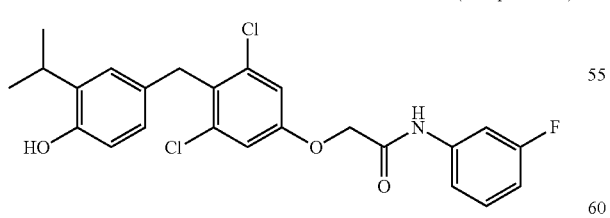

The titled compound was prepared according to the procedure of Example 1, substituting 3-fluoroaniline for ethylamine. MS(ES-API) m/z 460.0/462.0.

Example 25

(Compound 50)

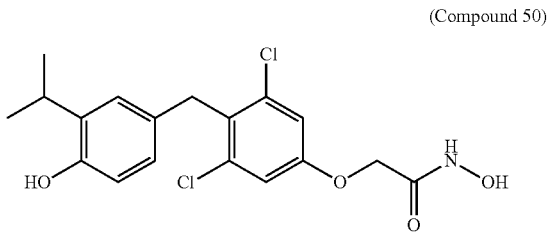

The titled compound was prepared according to the procedure of Example 1, substituting hydroxylamine (as an aqueous solution) for ethylamine. MS(ES-API) m/z 382.0/384.0.

Example 26

(Compound 53)

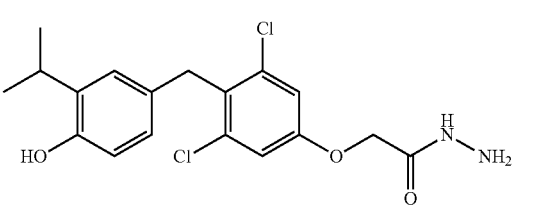

The titled compound was prepared according to the procedure of Example 1, substituting hydrazine (as an aqueous solution) for ethylamine. MS(ES-API) m/z 381.0/383.0.

Example 27

(Compound 56)

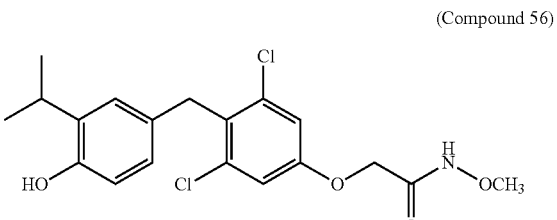

The titled compound was prepared according to the procedure of Example 1, substituting methoxylamine hydrochloride for ethylamine. MS(ES-API) m/z 398.1/400.0.

Example 28

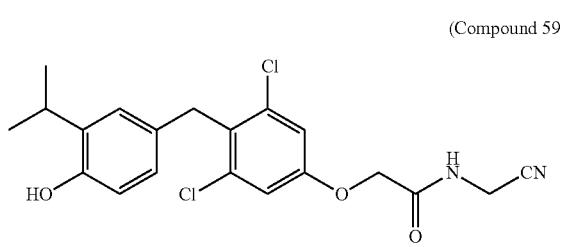 [SMILES: CCNC(=O)COc1cc(Cl)c(Cc2ccc(O)c(C(C)C)c2)c(Cl)c1]
(Compound 59)

The titled compound was prepared according to the procedure of Example 1, substituting aminoacetonitrile for ethylamine. MS(ES-API) m/z 405.0/407.0.

Example 29

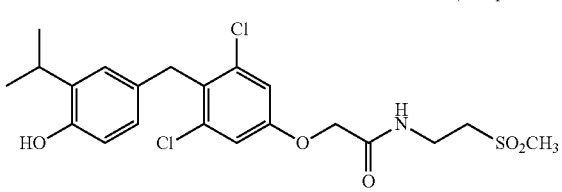
(Compound 62)

The titled compound was prepared according to the procedure of Example 1, substituting methyl-(2-aminoethyl)sulfone for ethylamine. MS(ES-API) m/z 473.9/475.8.

Example 30

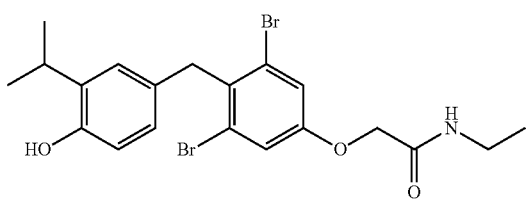
(Compound 3)

To a solution of Intermediate 10 (250 mg) in THF (10 mL) were added ethylamine (3 eq), EDCI, HOBt, and diisopropylamine (1.5 eq each). The reaction was stirred overnight at room temperature. The mixture was diluted with water (10 mL), extracted with EtOAc (10 mL*3). The combined EtOAc phase was washed by brine (10 mL), dried over $Na_2SO_4$, concentrated under reduce pressure and purified by prep-HPLC (ACN/water range from 30/70 to 85/15) to afford the titled compound as white solid. MS(ES-API) m/z 486.0

Example 31

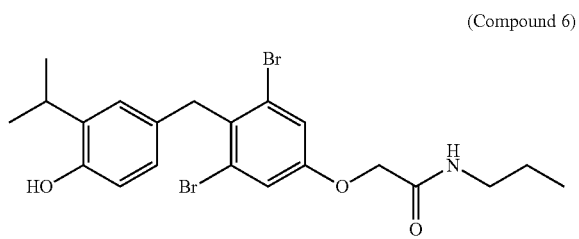 [SMILES: CCCNC(=O)COc1cc(Cl)c(Cc2ccc(O)c(C(C)C)c2)c(Cl)c1]
(Compound 6)

The titled compound was prepared according to the procedure of Example 30, substituting n-propylamine for ethylamine. MS(ES-API) m/z 499.9.

Example 32

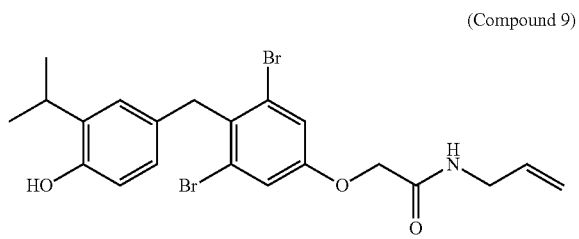 [SMILES: C=CCNC(=O)COc1cc(Cl)c(Cc2ccc(O)c(C(C)C)c2)c(Cl)c1]
(Compound 9)

The titled compound was prepared according to the procedure of Example 30, substituting allylamine for ethylamine. MS(ES-API) m/z 497.9.

Example 33

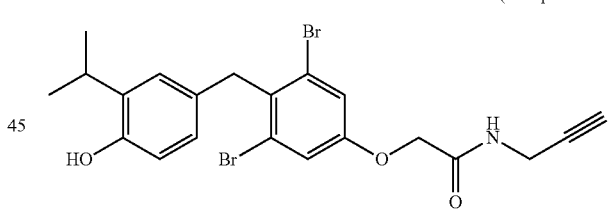
(Compound 12)

The titled compound was prepared according to the procedure of Example 30, substituting propargylamine for ethylamine. MS(ES-API) m/z 495.9.

Example 34

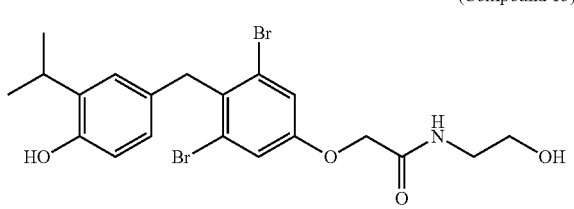
(Compound 15)

The titled compound was prepared according to the procedure of Example 30, substituting 2-aminoethanol for ethylamine. MS(ES-API) m/z 501.9.

Example 35

(Compound 21-R)

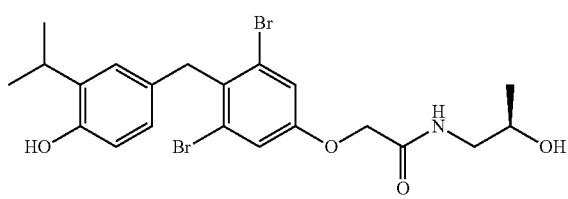

The titled compound was prepared according to the procedure of Example 30, substituting (R)-(−)-1-amino-2-propanol for ethylamine. MS(ES-API) m/z 515.8

Example 36

(Compound 21-S)

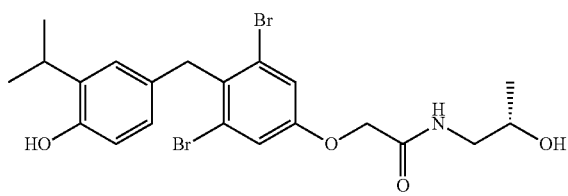

The titled compound was prepared according to the procedure of Example 30, substituting (S)-(+)-1-amino-2-propanol for ethylamine. MS(ES-API) m/z 515.9.

Example 37

(Compound 18-R)

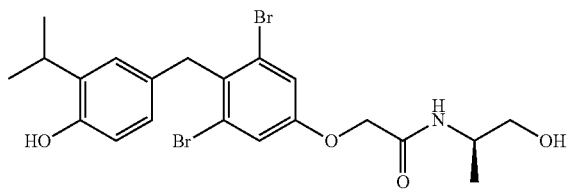

The titled compound was prepared according to the procedure of Example 30, substituting (R)-(−)-2-amino-1-propanol for ethylamine. MS(ES-API) m/z 515.9.

Example 38

(Compound 18-S)

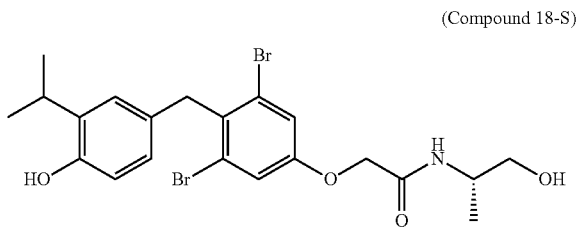

The titled compound was prepared according to the procedure of Example 30, substituting (S)-(+)-2-amino-1-propanol for ethylamine. MS(ES-API) m/z 515.9.

Example 39

(Compound 24)

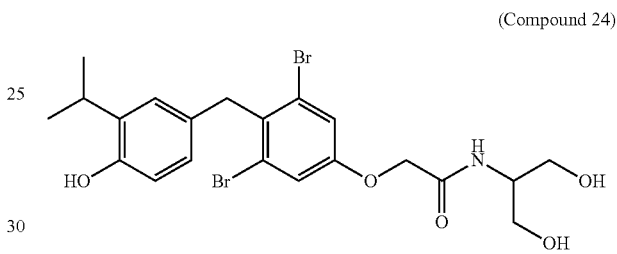

The titled compound was prepared according to the procedure of Example 30, substituting 2-amino-1,3-propane-diol for ethylamine. MS(ES-API) m/z 529.8.

Example 40

(Compound 27)

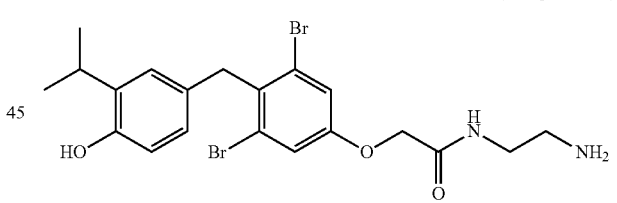

The titled compound was prepared according to the procedure of Example 30, substituting ethylenediamine for ethylamine. MS(ES-API) m/z 500.9.

Example 41

(Compound 30)

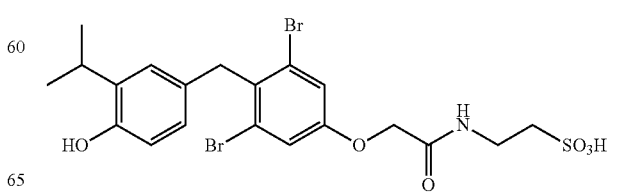

The titled compound was prepared according to the procedure of Example 30, substituting 2-aminoethanesulfonic acid for ethylamine. MS(ES-API) m/z 563.8.

Example 42

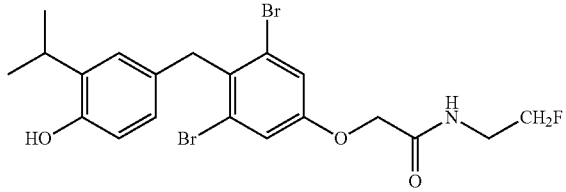
(Compound 33)

The titled compound was prepared according to the procedure of Example 30, substituting 2-fluoroethylamine for ethylamine. MS(ES-API) m/z 503.9.

Example 43

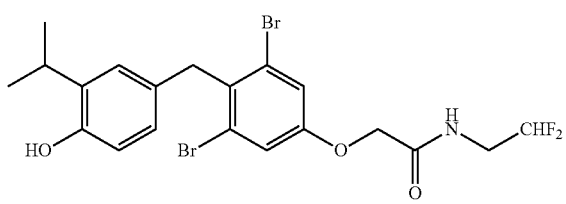
(Compound 36)

The titled compound was prepared according to the procedure of Example 30, substituting 2,2-difluoroethylamine for ethylamine. MS(ES-API) m/z 519.8.

Example 44

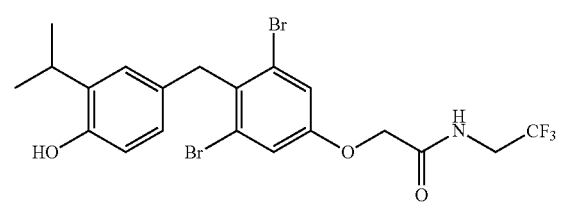
(Compound 39)

The titled compound was prepared according to the procedure of Example 30, substituting 2,2,2-trifluoroethylamine for ethylamine. MS(ES-API) m/z 537.9.

Example 45

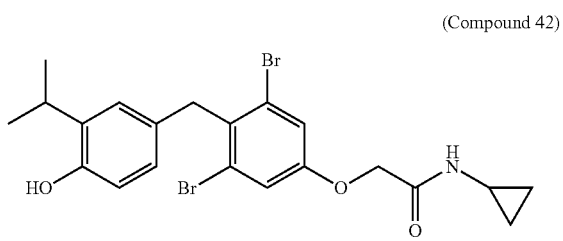 [SMILES: CC(C)c1cc(Cc2c(Cl)cc(OCC(=O)NC3CC3)cc2Cl)ccc1O]
(Compound 42)

The titled compound was prepared according to the procedure of Example 30, substituting cyclopropylamine for ethylamine. MS(ES-API) m/z 497.9.

Example 46

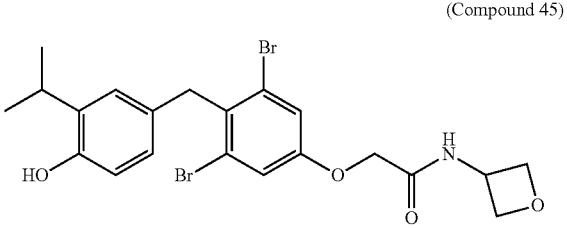 [SMILES: CC(C)c1cc(Cc2c(Cl)cc(OCC(=O)NC3COC3)cc2Cl)ccc1O]
(Compound 45)

The titled compound was prepared according to the procedure of Example 30, substituting 3-aminooxetane for ethylamine. MS(ES-API) m/z 513.9.

Example 47

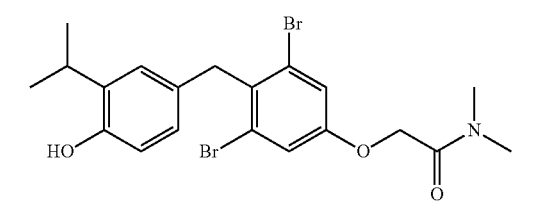
(Compound 48)

The titled compound was prepared according to the procedure of Example 30, substituting dimethylamine for ethylamine. MS(ES-API) m/z 485.9

Example 48

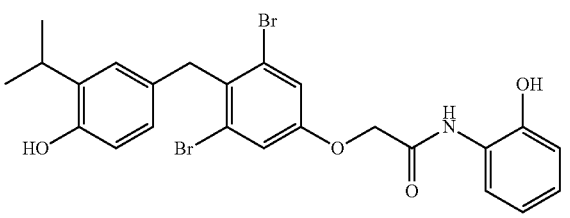
(Compound 66)

The titled compound was prepared according to the procedure of Example 30, substituting 2-hydroxyaniline for ethylamine. MS(ES-API) m/z 547.8.

Example 49

(Compound 69)

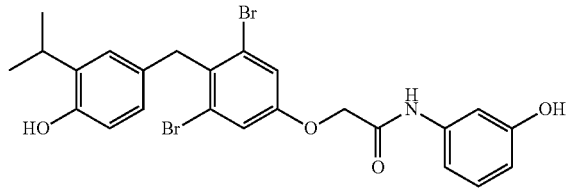

The titled compound was prepared according to the procedure of Example 30, substituting 3-hydroxyaniline for ethylamine. MS(ES-API) m/z 547.9.

Example 50

(Compound 75)

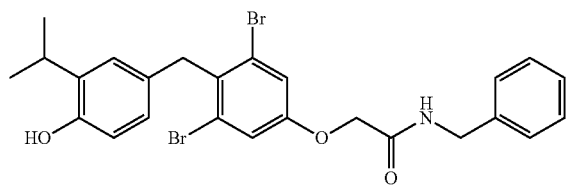

The titled compound was prepared according to the procedure of Example 30, substituting benzylamine for ethylamine. MS(ES-API) m/z 547.8.

Example 51

(Compound 78)

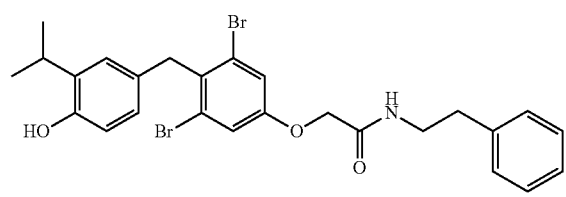

The titled compound was prepared according to the procedure of Example 30, substituting 2-phenethylamine for ethylamine. MS(ES-API) m/z 559.9.

Example 52

(Compound 81)

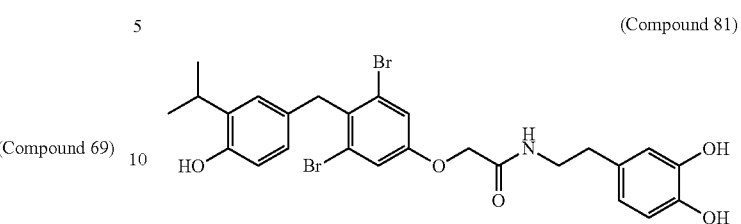

The titled compound was prepared according to the procedure of Example 30, substituting 2-(3,4-dihydroxy)phenethylamine for ethylamine. MS(ES-API) m/z 591.9.

Example 53

(Compound 72)

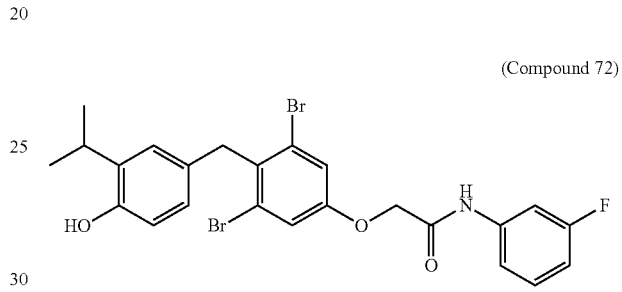

The titled compound was prepared according to the procedure of Example 30, substituting 3-fluoroaniline for ethylamine. MS(ES-API) m/z 549.9.

Example 54

(Compound 51)

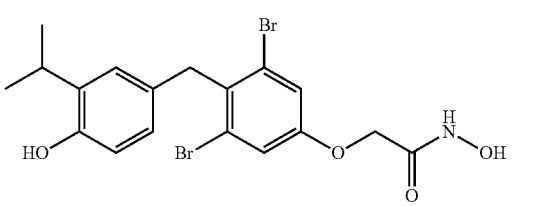

The titled compound was prepared according to the procedure of Example 30, substituting hydroxylamine (as an aqueous solution) for ethylamine. MS(ES-API) m/z 471.8.

Example 55

(Compound 54)

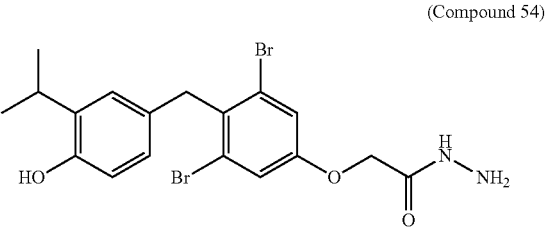 [SMILES: CC(C)c1cc(Cc2c(Br)cc(OCC(=O)NN)cc2Br)ccc1O]

The titled compound was prepared according to the procedure of Example 30, substituting hydrazine (as an aqueous solution) for ethylamine. MS(ES-API) m/z 472.8.

Example 56

(Compound 57)

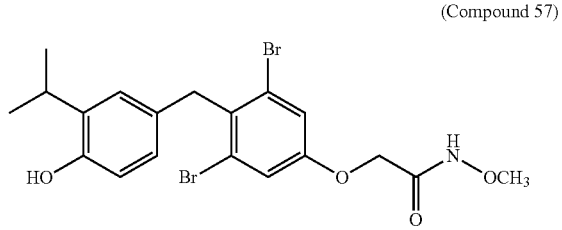 [SMILES: CONC(=O)COc1cc(Br)c(Cc2ccc(O)c(C(C)C)c2)c(Br)c1]

The titled compound was prepared according to the procedure of Example 30, substituting methoxylamine hydrochloride for ethylamine. MS(ES-API) m/z 487.9.

Example 57

(Compound 60)

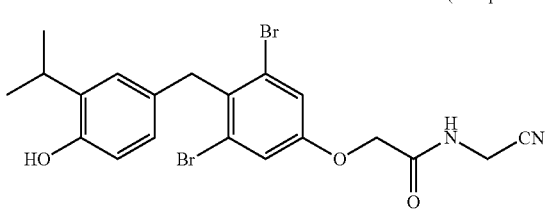

The titled compound was prepared according to the procedure of Example 30, substituting aminoacetonitrile for ethylamine. MS(ES-API) m/z 494.9.

Example 58

(Compound 63)

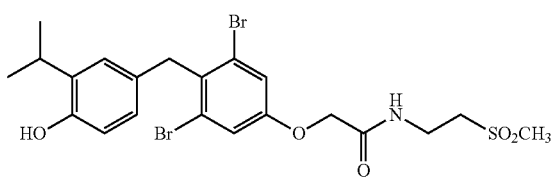

The titled compound was prepared according to the procedure of Example 30, substituting methyl-(2-aminoethyl)sulfone for ethylamine. MS(ES-API) m/z 561.9.

Example 59

Tissue Distribution Screen

For tissue concentration studies in male C57/BL6 mice, test compounds were formulated as NMP/solutol/PBS solution, at a concentration of 0.05 mg/mL and dosed at 2 mL/kg with the targeted dose of 0.100 mg/kg via SC injection. Plasma, brain, liver and other selected tissue samples were collected at 1 hr post-dose with three animals per time point.

As mentioned above, amide compounds of the present invention may act as substrates for the specific hydrolase enzyme fatty acid-amide hydrolase (FAAH), which cleaves the amide, liberating the thyromimetic. Thus, prodrug conversion to drug is enhanced in tissues that express high levels of FAAH such as the central nervous system. Tissue homogenates and plasma concentrations of the drug (from converted prodrug) were determined using LC-MS/MS with lower limits of quantitation of 0.0200-0.0500 ng/mL or 0.100-0.500 ng/g. The concentration ratios of tissue to plasma were determined and are reported in Table 2.

TABLE 2

Tissue Distribution of Representative Compounds

| Example # | Cpd. # | Plasma drug level (ng/ml) | Brain drug level (ng/g) | Liver drug level (ng/g) |
|---|---|---|---|---|
| 1 | 2 | 2.5 | 12 | 19 |
| 2 | 5 | 1.2 | 3.9 | 8 |
| 3 | 8 | 2.8 | 11 | 23 |
| 4 | 11 | 7.7 | 16 | 68 |
| 5 | 14 | 3.2 | 3.2 | 32 |
| 6 | 20-R | 2.4 | 2.9 | 19 |
| 7 | 20-S | 1.7 | 1.8 | 13 |
| 8 | 17-R | 1.6 | 2.2 | 13 |
| 9 | 17-S | 3.6 | 3.2 | 28 |
| 10 | 23 | 1.7 | 0.17 | 20 |
| 11 | 26 | 0.09 | 0.13 | 1.2 |
| 12 | 29 | 1.2 | <0.1 | 24 |
| 13 | 32 | 6.7 | 18 | 56 |
| 14 | 35 | 9.6 | 16 | 55 |
| 15 | 38 | 6.6 | 9.9 | 35 |
| 16 | 41 | 6.0 | 19 | 48 |
| 17 | 44 | 8.5 | 15 | 81 |
| 18 | 47 | 5.3 | 30 | 44 |
| 19 | 65 | 11 | 3.2 | 87 |
| 20 | 68 | 14 | 2.3 | 110 |
| 21 | 74 | 0.87 | 3.1 | 5.9 |
| 22 | 77 | 0.50 | 1.2 | 3.3 |
| 23 | 80 | 0.20 | 0.38 | 1.8 |
| 24 | 71 | 5.2 | 0.98 | 32 |
| 25 | 50 | 27 | 2.6 | 180 |
| 26 | 53 | 13 | 21 | 110 |
| 27 | 56 | 31 | 4.4 | 210 |
| 28 | 59 | 6.5 | 5.5 | 62 |
| 29 | 62 | 2.8 | 0.58 | 23 |
| 30 | 3 | 6.0 | 11 | 39 |
| 42 | 33 | 6.0 | 12 | 30 |

Example 60

Further Animal Assays

Transactivation Assay.

Human epithelial kidney cells (HEK 293) are grown to 80% confluency in Dubelcco's modified Eagles 4.5 g/L glucose medium (high glucose DMEM) containing 10% fetal bovine serum, 50 units/mL penicillin and 50 μg/mL streptomycin. The cells are trypsinized with 0.25% trypsin, then diluted to $5\times10^5$ cells/mL with high glucose DMEM. Cells are added to Costar 3917 96-well plates at $5\times10^4$ cells/well, then incubated at 37° C. for 24 hours. 1.5 μg of TR expression vector (full length TRα-CMV or TRβ-CMV), 1.5 μg of a reporter plasmid containing a DR4 thyroid hormone response element (TRE) direct repeat spaced by four nucleotides (AGGTCAcaggAGGTCA (SEQ ID NO:1)) cloned upstream of a minimal thymidine kinase promoter linked to a firefly luciferase coding sequence, and 0.75 μg of a pRL-SV40 constitutive Renilla luciferase reporter plasmid are diluted into 540 μL of OptiMEM. 27 μL of lipofectamine reagent was diluted into 540 μL of OptiMEM. The plasmid and lipofectamine dilutions are combined then incubated at RT for 10 min. The mixture was then diluted into 4.29 mL of OptiMEM. Plates are washed with 100 µL of phosphate buffered saline (PBS) at pH 7.2 without magnesium or calcium chloride per well. Transfection mixtures are added at 50 µL per well, then incubated at 37° C. for 4 hours. Modified DME/F-12 Ham's medium without phenol red containing 15 mM HEPES and bicarbonate, 5 mM L-glutamine, charcoal-stripped FBS, 50 units/mL penicillin and 50 µg/mL streptomycin was added at 50 µL per well, then the plates are incubated at 37° C. for 20 hours. Drug stocks are made at 10 mM in DMSO, then serially diluted to 1× concentrations in DME/F-12 Ham's. Plates are washed with 100 µL of PBS (pH 7.2) per well. 100 µL of each drug stock was added to the wells in triplicate, and then the plates are incubated at 37° C. for 24 hours.

Cells are assayed for luciferase activity using the Promega DualGlo kit. 50 µl of Luciferase Reagent are added per well, the plate was rocked for 15 min at RT, and then the plate was read for firefly luciferase activity. A 50 µl volume of Stop & Glo Reagent was added per well, then the plate was read for *Renilla* luciferase activity. Data normalized to *Renilla* internal control are analyzed with GraphPad Prism v.4a using the sigmoid dose response model to generate $EC_{50}$ values±SEM.

Animal Studies.

Experimental protocols are in compliance with the National Institutes of Health Guide for the Care and Use of Laboratory Animals and approved by the Oregon Health & Science University Institutional Animal Care & Use Committee. Wild type male C57BL/6J mice, aged 8-10 weeks, are housed in a climate controlled room with a 12 hour light-dark cycle with ad libitum access to food and water.

Distribution Studies.

Mice are injected once intraperitoneally (ip) with GC-1 at 9.14 µmol/kg, and analogs at 0.914, 9.14, and 30.5 µmol/kg. Euthanasia was performed on three mice per dose at 1 hr and the tissues and blood are harvested. Tissues are immediately frozen and blood was kept on ice for a minimum of 30 minutes and then spun down at 7,500×G for 15 minutes. Serum (100 uL) was collected and was stored with tissues at −80° C. until samples are processed.

Serum Processing.

The serum samples are warmed to RT and 10 uL of 2.99 µM internal standard (D6-GC-1) was added to them. Acetonitrile (500 uL) was added and the sample was vortexed for 20 seconds. The sample was then centrifuged at 10,000×G for 15 minutes at 4° C. Next, 90% of the upper supernatant was transferred to a glass test tube and concentrated using a speedvac for 1.5 hr at 45° C. The dried sample was then dissolved in 400 µL of 50:50 ACN:H2O and vortexed for 20 seconds. The resulting mixture was transferred to an Eppendorf tube and centrifuged at 10,000×G for 15 minutes. The supernatant was filtered with 0.22 µM centrifugal filters and submitted for LCMS/MS analysis. The standard curve was made with 100 µL of serum from a 8-10 week old mouse not injected with T3, GC-1, or analogs. The processing was performed exactly the same except after filtering the sample was split among 6 vials. GC-1, JD-20, and JD-21 are added to 5 of the 6 vials to make final concentrations of each compound in matrix of (0.1 pg/µL, 1 pg/µL, 10 pg/µL, 100 pg/µL, and 1000 pg/µL).

Brain Processing.

The brain samples are warmed to RT and transferred to a homogenizer tube with 5 GoldSpec ⅛ chrome steel balls (Applied Industrial Technologies). The resulting tube was weighed and then 1 mL of H2O was added, followed by 10 µL, of 2.99 µM internal standard (D6-Sobetirome). The tube was homogenized with a Bead Bug for 30 seconds and then transferred to a Falcon® tube containing 3 mL of ACN. A 1 ml volume of ACN was used to wash the homogenizer tube. Then the solution was transferred back to the Falcon® tube. The sample was then processed using the same method for the serum processing described above except the sample was concentrated in a glass tube using a speed vac for 4 hr at 45° C.

Gene Activation.

Mice are injected once intraperitoneally (ip) with vehicle (1:1 saline/DMSO), T3 at 0.305 µmol/kg, GC-1 at 9.14 µmol/kg, and analogs at 0.914, 9.14, and 30.5 µmol/kg. Euthanasia was performed on three mice per dose at 2 hr and the tissues are harvested. The brain tissues collected for qPCR analysis are processed according to a protocol for RNA extraction using Trizol reagent and the PureLink RNA mini kit, using Qiagen RNase-free DNase kit during the optional DNase treatment step. 1 µg of extracted RNA was used to synthesize cDNA via a reverse transcription (RT) reaction using the Qiagen QuantiTect Reverse Transcription kit. DNA contamination was controlled for by duplicating one sample without the addition of RT enzyme. Expression of the Hairless (Hr) gene was measured by QPCR using the QuantiTect SYBR green PCR kit from Qiagen. The primer sequences for hairless (Fwd: CCAAGTCTGGGC-CAAGTTTG (SEQ ID NO:2); Rev: TGTCCTTGGTCC-GATTGGAA (SEQ ID NO:3)) are previously described by Barca-Mayo19. The template cDNA was diluted 2-fold to minimize the interference of RT reagents in the qPCR reaction. Glyceraldehyde-3-Phosphate Dehydrogenase (GAPDH) was the housekeeping gene used for normalizing between samples. Data analysis for single dose experiment was done using the comparative CT method to look at the relative differences in Hr gene expression. Data analysis for dose-response experiment was done using GraphPad Prism v.4a with the sigmoid dose response model to generate $EC_{50}$ values±SEM.

Chemistry General.

$^1$H NMR are taken on a Bruker 400. All $^1$H NMR are calibrated to the NMR solvent reference peak (D6-acetone, CDCl3). Anhydrous tetrahydrofuran (THF) and dimethylformamide (DMF) are obtained from a Seca Solvent System. All other solvents used are purchased from Sigma-Aldrich or Fisher. Purity analysis of final compounds was determined to be >95% by HPLC. HPLC analysis was performed on a Varian ProStar HPLC with an Agilent Eclipse Plus C18 5 µM column (4.6×250 mm) with a gradient of 10% to 95% acetonitrile (0.1% TFA) over 15 minutes.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A compound having the structure of Formula (I):

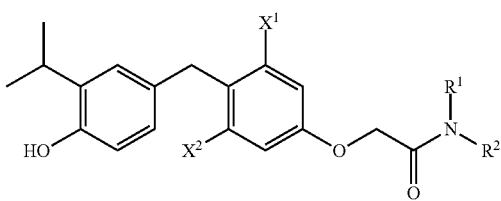

(I)

or a pharmaceutically acceptable isomer, racemate, hydrate, solvate, isotope or salt thereof, wherein:

$X^1$ and $X^2$ are independently selected from the group consisting of chlorine and bromine;

$R^1$ and $R^2$ are independently hydrogen, —$OR^a$, —$NR^aR^b$, $C_1$-$C_6$ alkyl, $C_2$-$C_6$ alkenyl, $C_2$-$C_6$ alkynyl, $C_3$-$C_6$ carbocycle, $C_3$-$C_6$ carbocylealkyl, $C_3$-$C_6$ heterocycle or $C_3$-$C_6$ heterocyclealkyl, wherein each $C_1$-$C_6$ alkyl, $C_3$-$C_6$ carbocycle, $C_3$-$C_6$ carbocylealkyl, $C_3$-$C_6$ heterocycle or $C_3$-$C_6$ heterocyclealkyl is optionally substituted with one or more of halo, cyano, —$OR^a$, —$NR^aR^b$, —$S(O)_2R^a$ or —$S(O)_2OR^a$; and each $R^a$ and $R^b$ is independently hydrogen or $C_1$-$C_6$ alkyl; with the proviso that when $R^1$ is hydrogen and both $X^1$ and $X^2$ are bromine or both $X^1$ and $X^2$ are chlorine, $R^2$ is not methyl.

2. The compound of claim 1 wherein $X^1$ and $X^2$ are both chlorine.

3. The compound of claim 1 wherein $X^1$ and $X^2$ are both bromine.

4. The compound of claim 1 wherein $X^1$ is chlorine and $X^2$ is bromine.

5. The compound of claim 1 wherein $X^1$ is bromine and $X^2$ is chlorine.

6. The compound of claim 1, wherein $R^1$ is hydrogen.

7. The compound of claim 1, wherein $R^2$ is hydrogen.

8. The compound of claim 1, wherein $R^2$ is —$OR^a$.

9. The compound of claim 1, wherein $R^2$ is —$NR^aR^b$.

10. The compound of claim 1, wherein $R^1$ and $R^2$ are alkyl.

11. The compound of claim 1, wherein $R^2$ is alkyl.

12. The compound of claim 11 wherein the alkyl is selected from the group consisting of methyl, ethyl, n-propyl, isopropyl, n-butyl, isobutyl, sec-butyl, tert-butyl, n-pentyl, branched pentyl, n-hexyl, and branched hexyl.

13. The compound of claim 1, wherein $R^2$ is alkenyl or alkynyl.

14. The compound of claim 1, wherein $R^2$ is propenyl.

15. The compound of claim 1, wherein $R^2$ is propynyl.

16. A compound of claim 1, wherein $R^2$ is alkyl substituted with one or more of halo, cyano, —$OR^a$, —$NR^aR^b$, —$S(O)_2R^a$ or —$S(O)_2OR^a$.

17. A compound of claim 1, wherein $R^2$ is $C_3$-$C_6$ carbocycle or $C_3$-$C_6$ carbocyclealkyl, each of which are optionally substituted with one or more of halo, cyano, —$OR^a$, —$NR^aR^b$, —$S(O)_2R^a$ or —$S(O)_2OR^a$.

18. A compound of claim 17 wherein $R^2$ is $C_3$-$C_6$ cycloalkyl optionally substituted with one or more of halo, cyano, —$OR^a$, —$NR^aR^b$, —$S(O)_2R^a$ or —$S(O)_2OR^a$.

19. The compound of claim 17 wherein $R^2$ is aryl optionally substituted with one or more of halo, cyano, —$OR^a$, —$NR^aR^b$, —$S(O)_2R^a$ or —$S(O)_2OR^a$.

20. The compound of claim 17 wherein $R^2$ is $C_3$-$C_6$ carbocylealkyl optionally substituted with one or more of halo, cyano, —$OR^a$, —$NR^aR^b$, —$S(O)_2R^a$ or —$S(O)_2OR^a$.

21. The compound of claim 1, wherein $R^2$ is $C_3$-$C_6$ heterocycle or $C_3$-$C_6$ heterocyclealkyl, each of which is optionally substituted with one or more of halo, cyano, —$OR^a$, —$NR^aR^b$, —$S(O)_2R^a$ or —$S(O)_2OR^a$.

22. The compound of claim 1 having the structure:

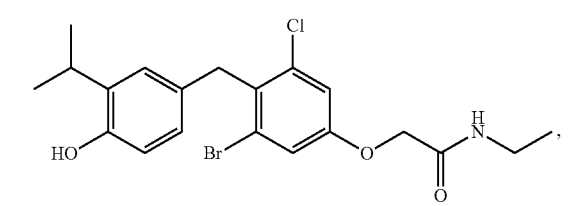

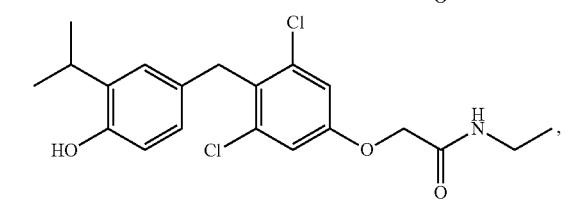

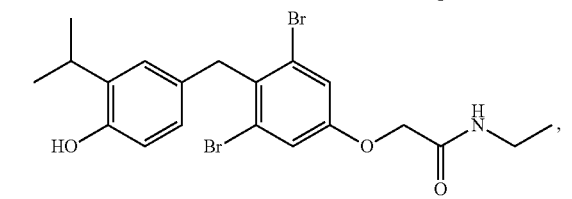

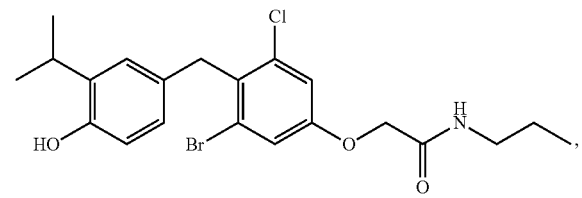

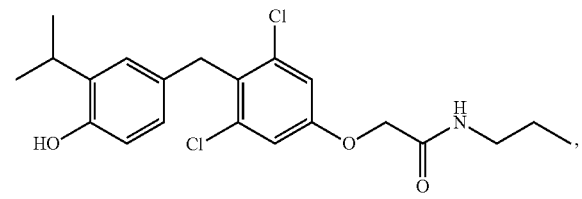

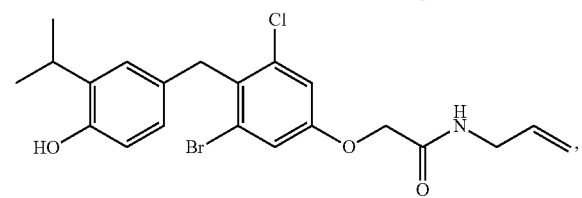

-continued

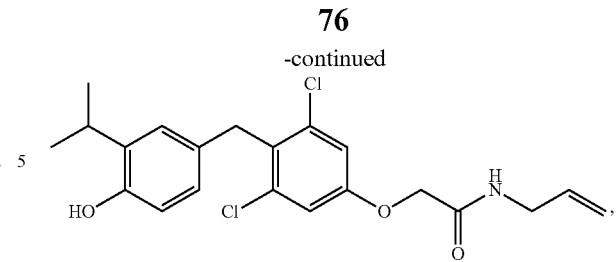

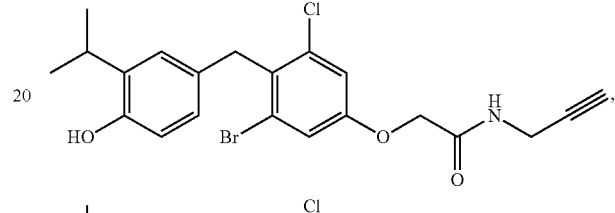

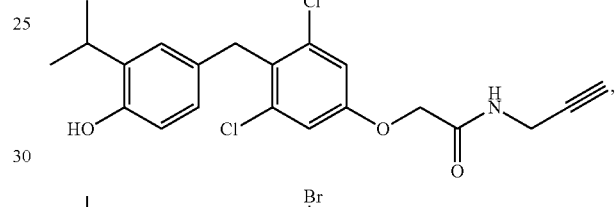

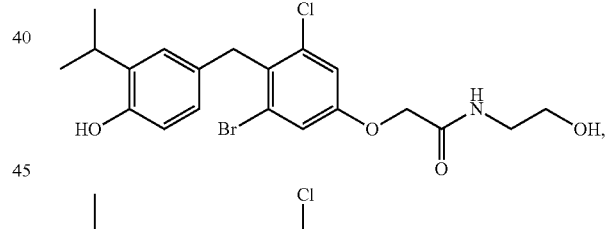

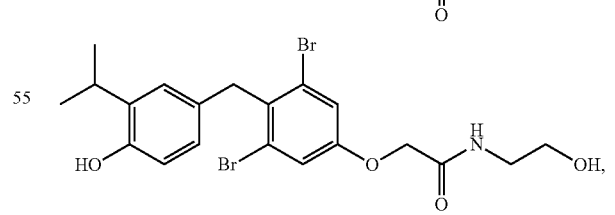

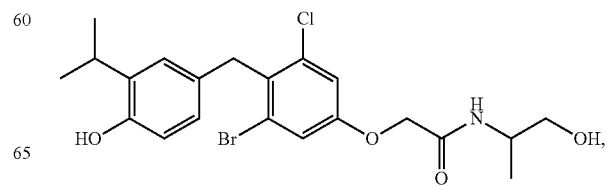

-continued

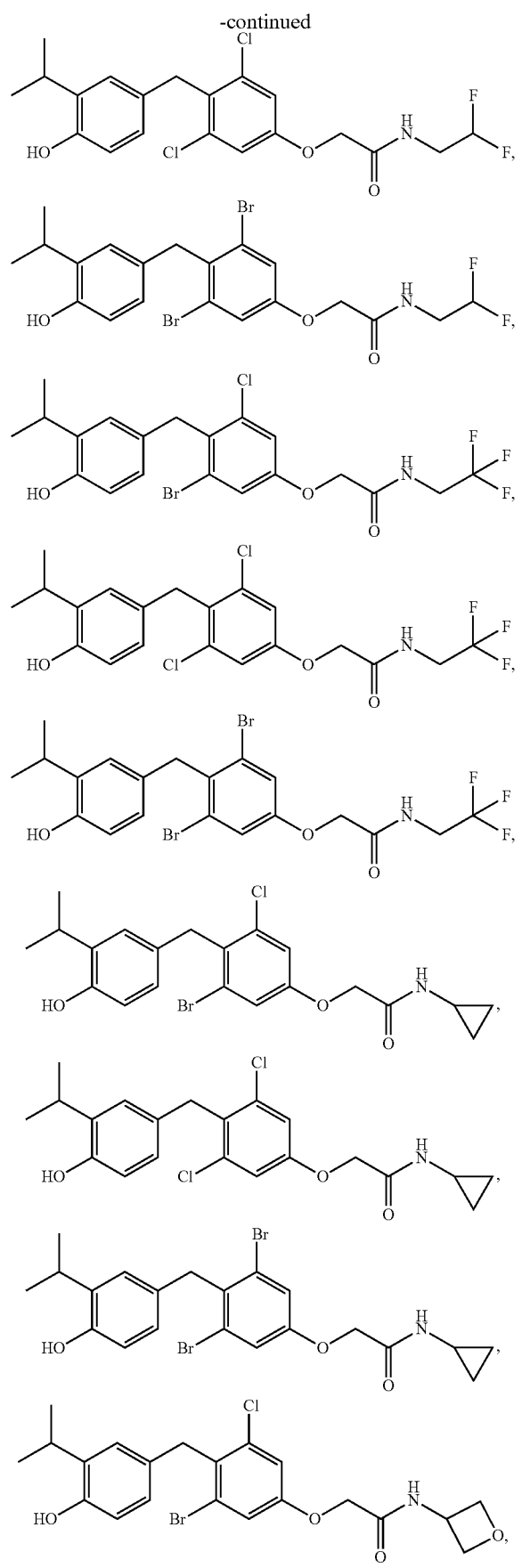
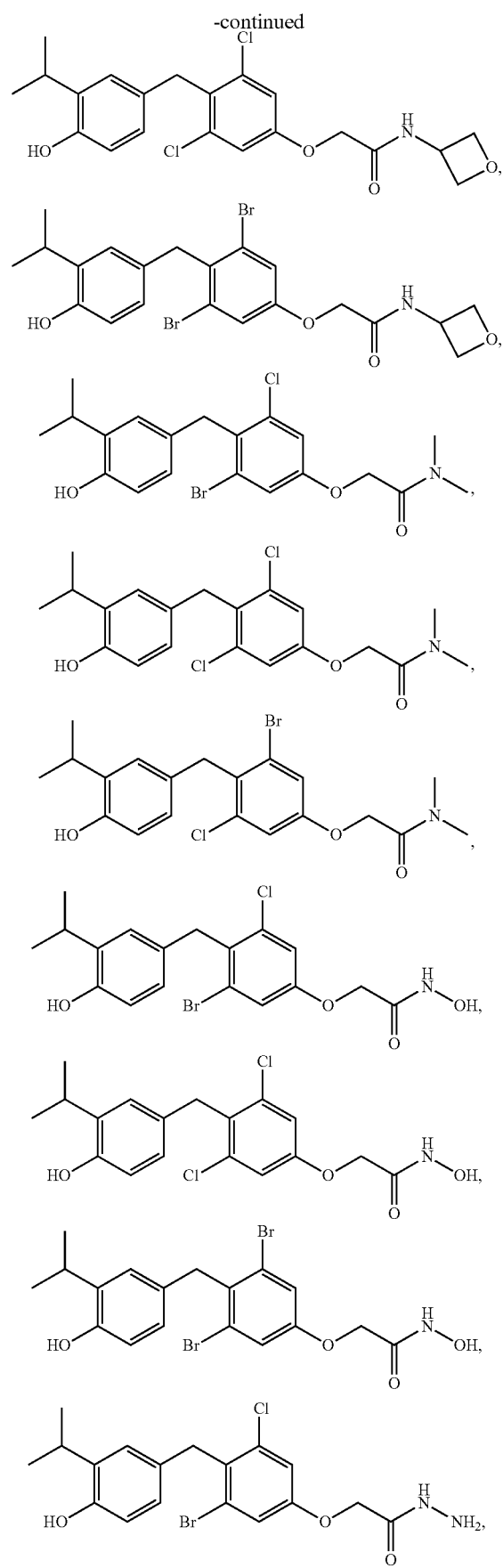

-continued
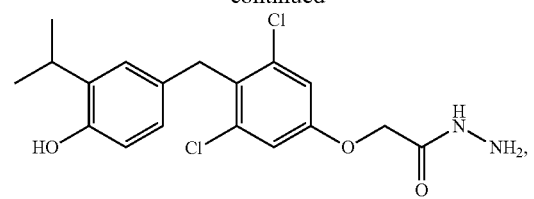
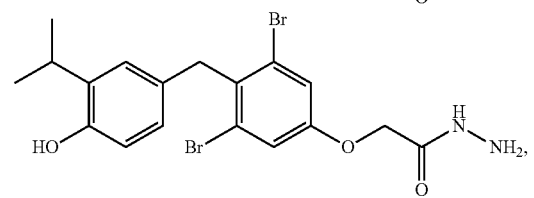
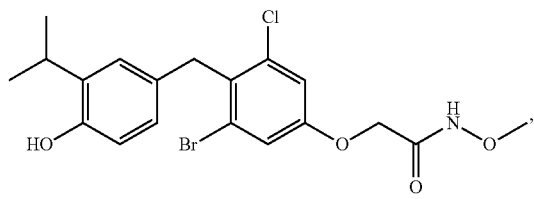
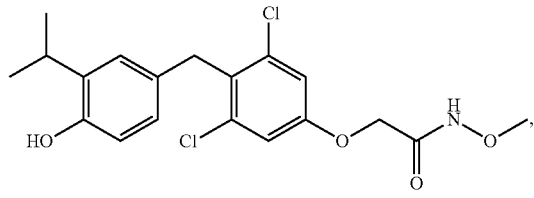
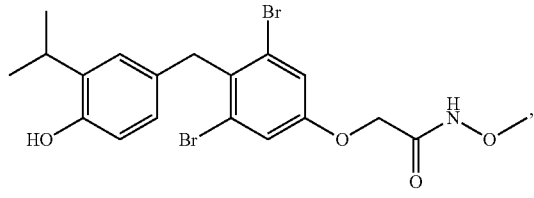
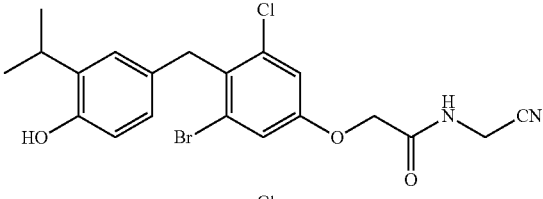
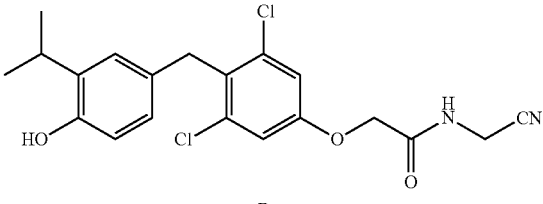
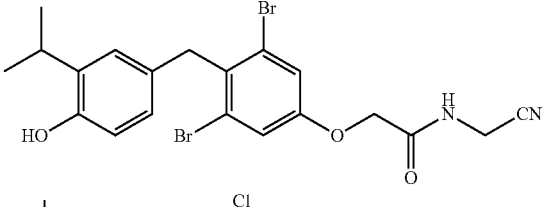
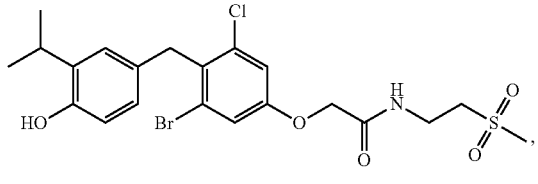
-continued
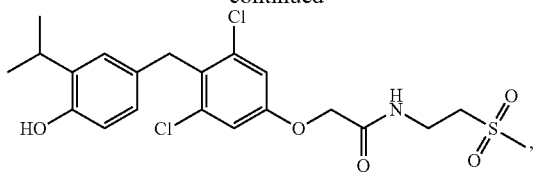
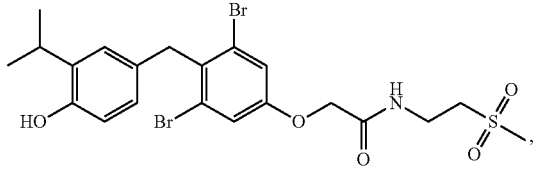
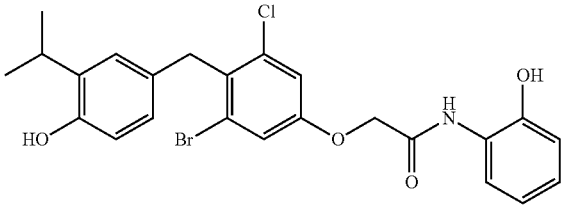
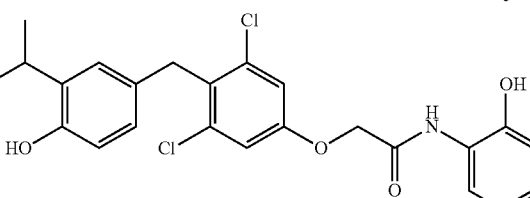
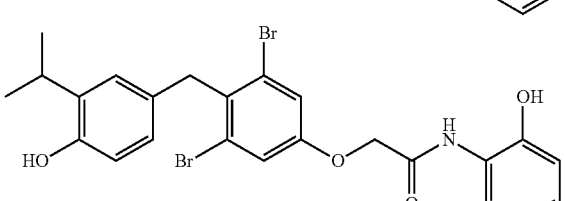
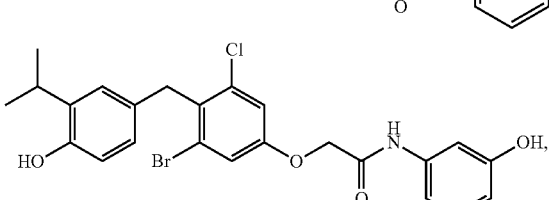
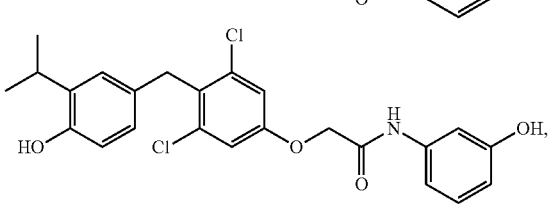
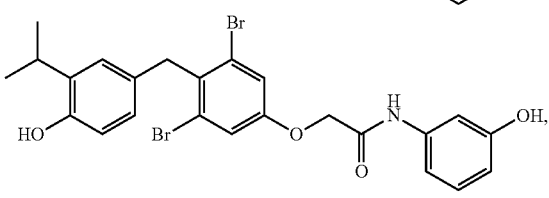
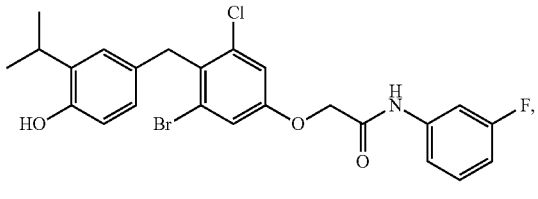

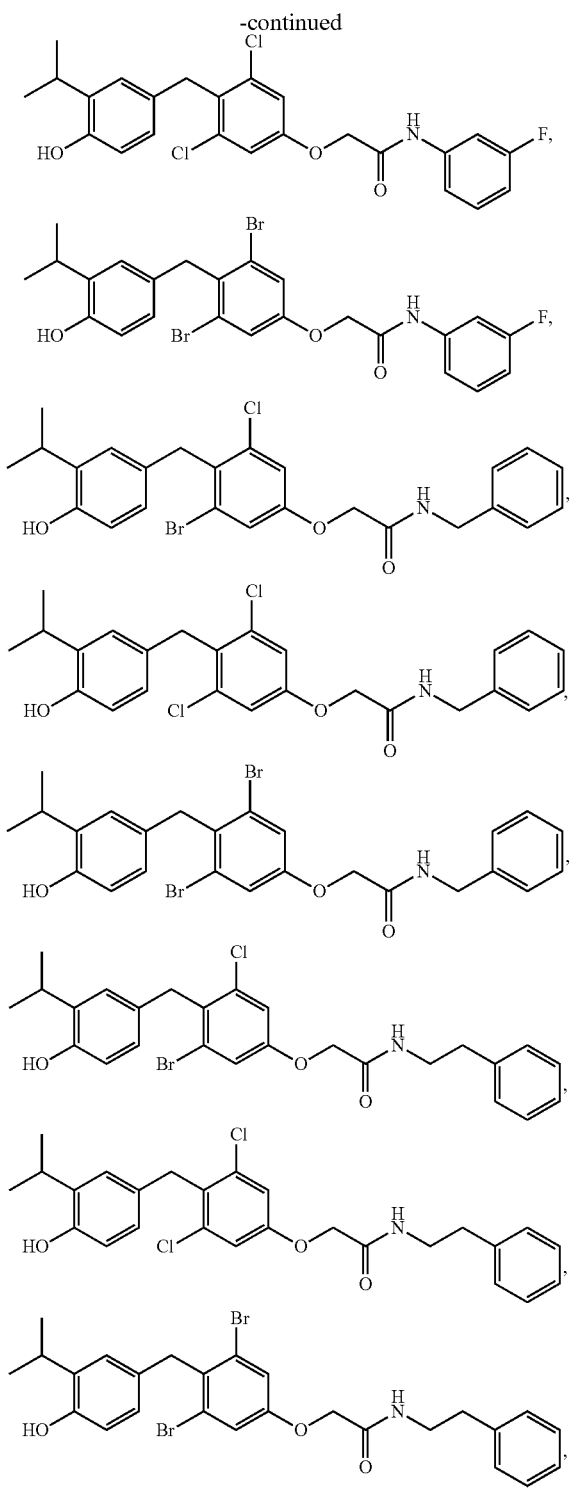

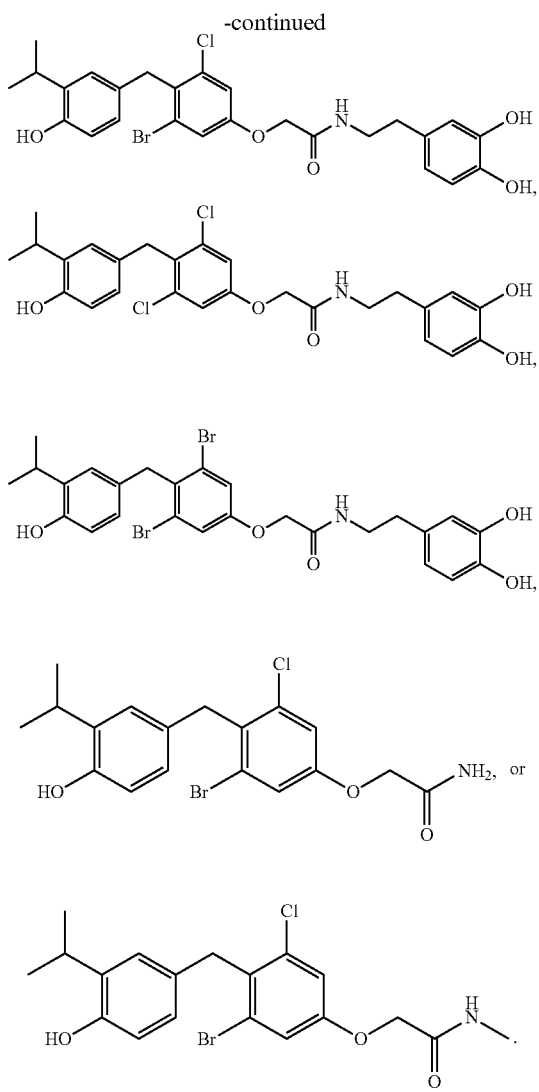

23. A pharmaceutical composition comprising a pharmaceutically effective amount of the compound of claim 1, or a pharmaceutically acceptable isomer, racemate, hydrate, solvate, isotope, or salt thereof, and one or more pharmaceutically acceptable carriers.

24. A method of treating a subject having a neurodegenerative disease, the method comprising: administering to the subject a pharmaceutically effective amount of the compound of claim 1, or a pharmaceutically acceptable isomer, racemate, hydrate, solvate, isotope, or salt thereof; wherein the neurodegenerative disease is demyelinating disease, X-linked adrenoleukodystrophy or multiple sclerosis.

* * * * *

SEQUENCE LISTING

```
<160> NUMBER OF SEQ ID NOS: 3

<210> SEQ ID NO 1
<211> LENGTH: 16
<212> TYPE: DNA
<213> ORGANISM: Artificial Sequence
<220> FEATURE:
<223> OTHER INFORMATION: Synthetic sequence

<400> SEQUENCE: 1
aggtcacagg aggtca                                               16

<210> SEQ ID NO 2
<211> LENGTH: 20
<212> TYPE: DNA
<213> ORGANISM: Artificial Sequence
<220> FEATURE:
<223> OTHER INFORMATION: Forward primer

<400> SEQUENCE: 2
ccaagtctgg gccaagtttg                                           20

<210> SEQ ID NO 3
<211> LENGTH: 20
<212> TYPE: DNA
<213> ORGANISM: Artificial Sequence
<220> FEATURE:
<223> OTHER INFORMATION: Reverse primer

<400> SEQUENCE: 3
tgtccttggt ccgattggaa                                           20
```